United States Patent [19]

Yamada et al.

[11] Patent Number: 5,668,286
[45] Date of Patent: Sep. 16, 1997

[54] OXAZOLIDINONE DERIVATIVES AND PHARMACEUTICAL COMPOSITIONS CONTAINING THEM

[75] Inventors: Hiroyoshi Yamada, Tsukuba; Kiyotaka Munesada, Shimotsuma; Mikio Taniguchi, Tsukuba, all of Japan

[73] Assignee: Pharmacia & Upjohn Company, Kalamazoo, Mich.

[21] Appl. No.: 714,117

[22] PCT Filed: Mar. 14, 1995

[86] PCT No.: PCT/US95/02972

§ 371 Date: Sep. 9, 1996

§ 102(e) Date: Sep. 9, 1996

[87] PCT Pub. No.: WO95/25106

PCT Pub. Date: Sep. 21, 1995

[30] Foreign Application Priority Data

| Mar. 15, 1994 | [JP] | Japan | 6-043949 |
| Jun. 28, 1994 | [JP] | Japan | 6-146565 |
| Sep. 29, 1994 | [JP] | Japan | 6-235167 |

[51] Int. Cl.$^6$ .................. A61K 31/445; C07D 211/46
[52] U.S. Cl. .................. 546/209; 540/603; 544/129; 544/364; 546/19; 546/208; 546/210
[58] Field of Search .................. 540/603; 544/129, 544/364; 546/19, 208, 209, 210

[56] References Cited

U.S. PATENT DOCUMENTS

| 4,476,136 | 10/1984 | Dostert et al. | 514/376 |
| 4,891,371 | 1/1990 | George et al. | 514/212 |
| 4,948,801 | 8/1990 | Carlson et al. | 514/307 |
| 5,523,403 | 6/1996 | Barbachyn | 544/137 |
| 5,547,950 | 8/1996 | Hutchinson et al. | 514/252 |
| 5,565,571 | 10/1996 | Barbachyn et al. | 546/144 |

FOREIGN PATENT DOCUMENTS

| 352781 | 1/1990 | European Pat. Off. |
| WO 93/09103 | 5/1993 | WIPO |
| WO93/23384 | 11/1993 | WIPO |

OTHER PUBLICATIONS

Park, C. et al, J. Med. Chem. 1992, 35, pp. 1156–65.

*Primary Examiner*—C. Warren Ivy
*Assistant Examiner*—Garth M. Dahlen
*Attorney, Agent, or Firm*—Lawrence T. Welch

[57] ABSTRACT

The present invention provides agents having high antimicrobial activity for preventing and treating infectious diseases. Thus, the present invention provides novel oxazolidinone derivatives represented by chemical formula (I), or pharmaceutically acceptable salts thereof, as well as antimicrobial compositions containing said derivatives or salts thereof as active ingredients.

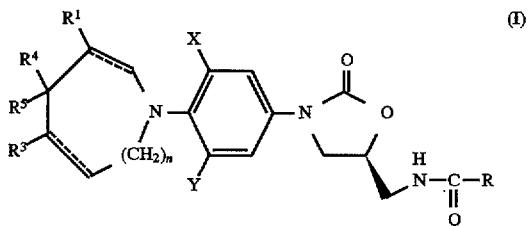

5 Claims, No Drawings

OXAZOLIDINONE DERIVATIVES AND PHARMACEUTICAL COMPOSITIONS CONTAINING THEM

This is the National Stage application of PCT/US95/02972 filed Mar. 14, 1995.

1. Field of Industrial Applicability

The present invention relates to novel oxazolidinone derivatives or pharmaceutically acceptable salts thereof, and pharmaceutical agents that contain them as active ingredients for preventing or treating infectious diseases.

More specifically, the present invention relates to useful antimicrobial agents effective against a number of human and veterinary pathogens, including multiply-resistant staphylococci and streptococci as well as anaerobic organisms such as bacteroides and clostridia species, and acid-fast organisms such as *Mycobacterium tuberculosis* and *Mycobacterium avium*.

2. Information Disclosure

International Publication No. WO93/23384 discloses oxazolidinones containing a substituted diazine (piperazine) moiety and their uses as antimicrobials. International Publication No. WO93/09103 discloses substituted aryl and heteroaryl-phenyl-oxazolidinones useful as antimicrobials. International Publication No. WO90/02744 discloses 5'-indolinyl-5β-amidomethyloxazolidinones, 3-(fused-ring substituted)phenyl-5β-amidomethyloxazolidinones, and 3-(nitrogen substituted)-phenyl-5β-amidomethyloxazolidinones which are useful as antibacterial agents.

Other references disclosing various oxazolidinones include U.S. Pat. No. 4,801,600, *J. Med. Chem.*, 32, 1673–81 (1989); *J. Med. Chem.*, 33, 2569–78 (1990); *Tetrahedron* 45, 1323–26 (1989); and *J. Med. Chem.*, 35, 1156 (1992).

European Patent Publication 352,781 discloses phenyl and pyridyl substituted phenyl oxazolidinones. European Patent Publication 316,594 discloses 3-substituted styryl oxazolidinones. European Patent Publication 312,000 discloses phenylmethyl and pyridylmethyl substituted phenyl oxazolidinones.

SUMMARY OF THE INVENTION

Problems to be Solved by the Invention

The object of the present invention is to provide novel oxazolidinone derivatives or pharmaceutically acceptable salts thereof which have high antimicrobial activities, and antimicrobial compositions that contain them as active ingredients.

Means for Solving the Problems

The present inventors conducted intensive studies in order to accomplish the above object. As a result, useful and novel oxazolidinone derivatives were found and the present invention has been accomplished on the basis of the finding.

The present invention provides an oxazolidinone derivative represented by the general formula (I):

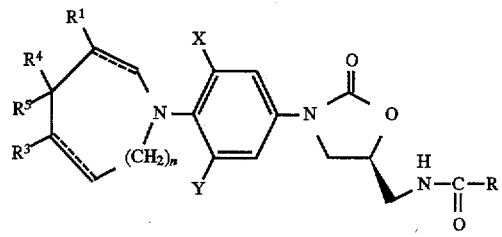

wherein
R is
  (a) hydrogen atom,
  (b) $C_1$–$C_8$ alkyl,
  (c) $C_3$–$C_6$ cycloalkyl,
  (d) amino,
  (e) $C_1$–$C_8$ alkylamino,
  (f) $C_1$–$C_8$ dialkylamino,
  (g) $C_1$–$C_8$ alkoxy, or
  (h) $C_1$–$C_8$ halogenoalkyl;

$R^1$ and $R^3$ are each and independently
  (a) hydrogen atom,
  (b) halogen atom,
  (c) $C_1$–$C_8$ alkyl,
  (d) $C_3$–$C_6$ cycloalkyl,
  (e) —$(CH_2)_m$—$OR^{11}$, or
  (f) —$C(=O)$—$R^{41}$;

X and Y are each and independently
  (a) hydrogen atom, or
  (b) halogen atom;

$R^4$ and $R^5$ are each and independently
  (a) hydrogen atom,
  (b) $C_1$–$C_8$ alkyl,
  (c) $C_1$–$C_8$ alkoxy,
  (d) $C_1$–$C_8$ alkylthio,
  (e) —$(CH_2)_m$—$OR^{51}$,
  (f) —O—$(CH_2)_m$—$OR^{51}$,
  (g) —$NR^{42}R^{52}$,
  (h) —N=CH—$NR^{44}R^{55}$,
  (i) —$C(=O)$—$NR^{42}R^{52}$, or
  (j) —$(CH_2)_m$—$C(=A)$—$R^{41}$, or they may combine together to form
  (k) =O,
  (l) =$NR^{43}$,
  (m) =S,
  (n) =$CR^{44}R^{54}$, or
  (o) an optionally substituted, unsaturated or saturated 5- or 6-membered hetero ring having 1–3 hetero atoms selected from the group consisting of a nitrogen atom, an oxygen atom and a sulfur atom;

$R^{11}$ and $R^{12}$ are each and independently
  (a) hydrogen atom,
  (b) $C_1$–$C_8$ alkyl, or
  (c) methoxymethyl;

$R^{41}$ is
  (a) hydrogen atom,
  (b) —$(CH_2)_m$—OH,
  (c) $C_1$–$C_8$ alkyl,
  (d) $C_1$–$C_8$ alkoxy,
  (e) —O—$CH_2$—O—$C(=O)$—$R^{11}$, or
  (f) —$(CH_2)_m$—$C(=O)$—$OR^{11}$;

$R^{42}$ and $R^{52}$ are each and independently
  (a) hydrogen atom,
  (b) —$(CH_2)_m$—$OR^{11}$,
  (c) $C_1$–$C_8$ alkyl, (d) —C(=O)—$R^{41}$,
(e) —C(=O)—$NR^{11}R^{12}$,
(f) —$(CH_2)_p$-phenyl,
(g) thiazol-2-yl, or they may combine together to form a pyrrolidino group, a piperidino group, a piperazino group, a morpholino group, or a thiomorpholino group, each of which may be substituted by $C_1$–$C_8$ alkyl or —$(CH_2)_m$—OH;

$R^{43}$ is
(a) hydrogen atom,
(b) —$OR^{51}$,
(c) $C_1$–$C_8$ alkyl,
(d) $C_1$–$C_8$ alkoxy,
(e) —$(CH_2)_p$-phenyl,
(f) —$NR^{42}R^{52}$,
(g) —NH—C(=NH)—$NH_2$,
(h) [1,2,4]triazol-4-yl, or
(i) cyano;

$R^{44}$ and $R^{54}$ are each and independently
(a) hydrogen atom,
(b) $C_1$–$C_8$ alkyl,
(c) —C(=O)—$R^{41}$, or
(d) —$(CH_2)_p$-phenyl;

$R^{51}$ is
(a) hydrogen atom,
(b) $C_1$–$C_8$ alkyl,
(c) $C_1$–$C_8$ alkyl substituted by one or more hydroxy,
(d) $C_2$–$C_8$ alkenyl,
(e) $C_1$–$C_8$ halogenoalkyl,
(f) —$(CH_2)_m$—$OR^{11}$,
(g) —$(CH_2)_m$—C(=O)—$R^{41}$,
(h) —C(=O)—$(CH_2)_m$—$OR^{44}$, or
(i) tosyl;

A is
(a) oxygen atom, or
(b) ethyleneketal;

⃛ is a double bond or a simple bond;

m's are each and independently 0, 1 or 2;

n is 0 or 1;

p's are each and independently 1, 2, 3 or 4;

and $C_1$–$C_8$ alkyl, in each of the above definitions, may be each and independently substituted by one or more substituents selected from the group consisting of a halogen atom, a hydroxy group, $C_1$–$C_8$ alkoxy group, $C_1$–$C_8$ acyloxy group, an amino group, $C_1$–$C_8$ alkylamino group, $C_1$–$C_8$ dialkylamino group, —CN group and a carboxyl group, or a pharmaceutically acceptable salt thereof.

The present invention also provides an antimicrobial agent that contains the oxazolidinone derivative or a pharmaceutically acceptable salt thereof as an effective ingredient. The antimicrobial agent containing the effective ingredient of the present invention can be used for treatment or prevention of infectious diseases. The term "treatment" as used herein means partial or total lessening of symptoms of a disease which a patient suffers from; the term "prevention" as used herein means partial or total avoidance of symptoms of a disease in a patient who, according to a doctor's diagnosis, may suffer from the disease or a related state unless the preventive measure is taken.

This invention provides novel oxazolidinone derivatives useful as preventatives and therapeutics for infectious diseases. The compounds of this invention have excellent antimicrobial action against various human and veterinary pathogens, including multiply-resistant staphylococci and streptococci, as well as anaerobic organisms such as bacteroides and clostridia species, and acid-fast *Mycobacterium tuberculosis* and *Mycobacterium avium*.

The carbon content of various hydrocarbon containing moieties is indicated by a prefix designating the minimum and maximum number of carbon atoms in the moiety, i.e., the prefix $C_i$–$C_j$ defines the number of carbon atoms present from the integer "i" to the integer "j" inclusive. Thus, $C_1$–$C_3$ alkyl refers to alkyl of 1–3 carbon atoms, inclusive, or methyl, ethyl, propyl, and isopropyl; $C_1$–$C_8$ alkyl is methyl, ethyl, propyl, butyl, pentyl, hexyl, heptyl, octyl and isomeric forms thereof.

$C_1$–$C_8$ alkyl in the general formula (I) for the compounds of the present invention refers to methyl, ethyl, propyl, butyl, pentyl, hexyl, heptyl, octyl and isomeric forms thereof; it means preferably methyl, ethyl, propyl, butyl, pentyl, hexyl and isomeric forms thereof, and more preferably methyl, ethyl, propyl, butyl and isomeric forms thereof.

The $C_1$–$C_8$ alkyl group may optionally be substituted by one or more substituents selected from the group consisting of a halogen atom, a hydroxy group, $C_1$–$C_8$ alkoxy group, $C_1$–$C_8$ acyloxy group, an amino group, $C_1$–$C_8$ alkylamino group, $C_1$–$C_8$ dialkylamino group, —CN group and a carboxyl group. Such substituted $C_1$–$C_8$ alkyl groups include 1-chloropropyl, 1-fuluoropropyl, 3-chloropropyl, 3-fuluoropropyl, hydroxymethyl, 3-hydroxypropyl, 2,3-dihydroxypropyl, 1-hydroxybutyl, 2-hydroxybutyl, 1-methoxypropyl, 1-octyloxypropyl, 1-acetoxypropyl, 1-aminopropyl, 1-aminooctyl, 1-butylaminopropyl, 1,1-dibutylaminopropyl, 1-cyanobutyl, 1-carboxybutyl and the like.

The term $C_2$–$C_8$ alkenyl means vinyl, 1-propenyl, 2-propenyl, 2-methyl-1-propenyl, 1-butenyl, 2-butenyl, 1-pentenyl, 2-pentenyl, 1-hexenyl, 1-heptenyl, 1-octenyl and isomeric forms thereof, preferably an alkenyl group having 2 to 6 carbon atoms, and more preferably an alkenyl group having 2 to 4 carbon atoms.

The term $C_3$–$C_6$ cycloalkyl means cyclopropyl, cyclobutyl, cyclopentyl or cyclohexyl.

The term $C_1$–$C_8$ alkylamino means an amino moiety containing one alkyl moiety having 1 to 8 carbon atoms, and the term $C_1$–$C_8$ dialkylamino means an amino moiety containing two alkyl moieties having 1 to 8 carbon atoms. For example, the two terms cover propylamino and dipropylamino, respectively; they mean preferably alkylamino and dialkylamino containing an alkyl moiety having 1 to 6 carbon atoms, and more preferably, alkylamino and dialkylamino containing an alkyl moiety having 1 to 4 carbon atoms.

The term $C_1$–$C_8$ alkoxy means methoxy, ethoxy, propoxy, butoxy, pentoxy, hexyloxy, heptyloxy, octyloxy and isomeric forms thereof, preferably an alkoxy group having 1 to 6 carbon atoms, and more preferably an alkoxy group having 1 to 4 carbon atoms. $C_1$–$C_8$ alkylthio means methythio, ethylthio, propylthio, butylthio, pentylthio, hexylthio, heptylthio, octylthio and isomeric forms thereof, preferably an alkylthio group having 1 to 6 carbon atoms, and more preferably an alkylthio group having 1 to 4 carbon atoms.

The halogen atom means a fluorine atom, a chlorine atom, a bromine atom or an iodine atom. Preferred halogen atom for X and Y is a fluorine atom.

The term $C_1$–$C_8$ halogenoalkyl means a $C_1$–$C_8$ alkyl group in which the hydrogen atoms are substituted by the halogen atom defined above; this is preferably a halogen substituted alkyl group having 1–6 carbon atoms, more preferably 1–4 carbon atoms. $C_1$–$C_8$ halogenoalkyl may be exemplified by fluoromethyl, trifluoromethyl, 2-fluoroethyl, 2-chloroethyl, 2,2,2-trifluoroethyl and 2,3-difluoropropyl.

The unsaturated or saturated 5- or 6-membered ring that is to be formed by $R^4$ and $R^5$ when taken together and which have 1–3 hetero atoms selected from the group consisting of a nitrogen atom, an oxygen atom and a sulfur atom may be exemplified by hetero rings such as [1,3]dioxane, [1,3] dioxolane(ethyleneketal), imidazolidine, [1,3]dithiolane, [1,3]oxathiolane, oxazolidine and 2,3-dihydrothiazole. The hetero ring may optionally be substituted by $C_1$–$C_4$ alkyl or acetyl which may optionally be substituted by one or more hydroxy groups, and each of said substituent hydroxy group may optionally be substituted by $C_1$–$C_4$ alkyl, methoxymethyl, ester and the like. The nitrogen atom forming the hetero rings may have a protective group such as an acetyl or hydroxyacetyl group. A preferred hetero ring within the definition is [1,3]dioxolane(ethyleneketal).

Where two variables are stated to be "each and independently" certain moieties, it is meant that each occurrence of each variable may be the same or different and will be selected from the moieties listed.

The term —$(CH_2)_p$-phenyl means preferably a benzyl group where p is 1.

The compounds of the present invention can be converted to their salts according to conventional methods.

Pharmaceutically acceptable salts means acid addition salts useful for administering the compounds of this invention and these include hydrochloride, hydrobromide, sulfate, phosphate, acetate, propionate, lactate, mesylate, maleate, succinate, tartrate, citrate, 2-hydroxyethyl sulfonate, fumarate and the like when a basic group is present. These salts may be in hydrated form. Some of the compounds of this invention may form metal salts such as sodium, potassium, calcium and magnesium salts and these are embraced by the term "pharmaceutically acceptable salts".

The preferred absolute configuration at C-5 of the oxazolidinone ring of compounds claimed in this invention is as represented in the structure of Formula (I). This absolute configuration is called (S) under the Cahn-Ingold-Prelog nomenclature system. It is this (S)-enantiomer which is pharmacologically active. The racemic mixture is useful in the same way and for the same purpose as the pure (S)-enantiomer; the difference is that twice as much racemic material must be used to produce the same antibacterial effect. Depending on substituents, the compounds of this invention may exist in geometric, optical and other isomeric forms and this invention embraces any of these isomers.

Particular preferred examples of the oxazolidinone derivatives represented by the general formula (I) are as follows (prefixed by compound numbers):

1) (S)-1-{4-[5-(acetylamino-methyl)-2-oxo-oxazolidin-3-yl]-2-fluoro-phenyl}-piperidine-4-carboxylic acid ethyl ester,
2) (S)-N-[3-(3-fluoro-4-piperidin-1-yl-phenyl)-2-oxo-oxazolidin-5-ylmethyl]-acetamide,
3) (S)-N-{3-[3-fluoro-4-(4-hydroxy-piperidin-1-yl)-phenyl]-2-oxo-oxazolidin-5-ylmethyl}-acetamide,
4) (S)-N-{3-[3-fluoro-4-(4-hydroxymethyl-piperidin-1-yl)-phenyl]-2-oxo-oxazolidin-5-ylmethyl}-acetamide,
5) (S)-N-{3-[4-(4-dibenzylamino-piperidin-1-yl)-3-fluoro-phenyl]-2-oxo-oxazolidin-5-ylmethyl}-acetamide,
6) (S)-N-{3-[4-(4-amino-piperidin-1-yl)-3-fluoro-phenyl]-2-oxo-oxazolidin-5-ylmethyl}-acetamide,
7) (S)-N-{3-[3-fluoro-4-(4-oxo-piperidin-1-yl)-phenyl]-2-oxo-oxazolidin-5-ylmethyl}-acetamide,
8) (S)-1-{4-[5-(acetylamino-methyl)-2-oxo-oxazolidin-3-yl]-2-fluoro-phenyl}-piperidine-4-carboxylic acid,
9) (S)-N-{3-[4-(4-acetylamino-piperidin-1-yl)-3-fluoro-phenyl]-2-oxo-oxazolidin-5-ylmethyl}-acetamide,
10) (S)-N-(1-{4-[5-(acetylamino-methyl)-2-oxo-oxazolidin-3-yl]-2-fluoro-phenyl}-piperidin-4-yl)-2-hydroxy-acetamide,
11) (S)-N-{3-[3-fluoro-4-(4-hydroxyimino-piperidin-1-yl)-phenyl]-2-oxo-oxazolidin-5-ylmethyl}-acetamide,
12) (S)-N-(3-{3-fluoro-4-[4-(2-oxo-propylidene)-piperidin-1-yl]-phenyl}-2-oxo-oxazolidin-5-ylmethyl)-acetamide,
13) (S)-N-{3-[4-(4-acetyl-piperidin-1-yl)-3-fluoro-phenyl]-2-oxo-oxazolidin-5-ylmethyl}-acetamide,
14) (S)-N-(3-{3-fluoro-4-[4-(2-hydroxy-acetyl)-piperidin-1-yl]-phenyl}-2-oxo-oxazolidin-5-ylmethyl)-acetamide,
15) (S)-N-{3-[3-fluoro-4-(4-oxo-azepan-1-yl)-phenyl]-2-oxo-oxazolidin-5-ylmethyl}-acetamide,
16) (S)-N-{3-[3-fluoro-4-(4-thioxo-piperidin-1-yl)-phenyl]-2-oxo-oxazolidin-5-ylmethyl}-acetamide,
17) (S)-N-{3-[3,5-difluoro-4-(4-oxo-piperidin-1-yl)-phenyl]-2-oxo-oxazolidin-5-ylmethyl}-acetamide,
18) (S)-N-{3-[3-fluoro-4-(3-fluoro-4-oxo-piperidin-1-yl)-phenyl]-2-oxo-oxazolidin-5-ylmethyl}-acetamide,
19) (S)-N-{3-[3-fluoro-4-(3-methyl-4-oxo-piperidin-1-yl)-phenyl]-2-oxo-oxazolidin-5-ylmethyl}-acetamide,
20) (S)-N-{3-[3-fluoro-4-(3-hydroxymethyl-5-methyl-4-oxo-piperidin-1-yl)-phenyl]-2-oxo-oxazolidin-5-ylmethyl}-acetamide,
21) (S)-N-{3-[3-fluoro-4-(4-methyl-piperidin-1-yl)-phenyl]-2-oxo-oxazolidin-5-ylmethyl}-acetamide,
22) (S)-N-{3-[3-fluoro-4-(4-methoxy-piperidin-1-yl)-phenyl]-2-oxo-oxazolidin-5-ylmethyl}-acetamide,
23) (S)-N-{3-[3-fluoro-4-(4-methylsulfanyl-piperidin-1-yl)-phenyl]-2-oxo-oxazolidin-5-ylmethyl}-acetamide,
24) (S)-N-{3-[4-(4-dimethylamino-piperidin-1-yl)-3-fluoro-phenyl]-2-oxo-oxazolidin-5-ylmethyl}-acetamide,
25) (S)-1-{4-[5-(acetylamino-methyl)-2-oxo-oxazolidin-3-yl]-2-fluoro-phenyl}-piperidine-4-carboxylic acid amide,
26) (S)-N-{3-[3-fluoro-4-(4-hydroxymethylimino-piperidin-1-yl)-phenyl]-2-oxo-oxazolidin-5-ylmethyl}-acetamide,
27) (S)-N-{3-[3-fluoro-4-(4-methylimino-piperidin-1-yl)-phenyl]-2-oxo-oxazolidin-5-ylmethyl}-acetamide,
28) (S)-N-{3-[3-fluoro-4-(3-hydroxy-4-oxo-piperidin-1-yl)-phenyl]-2-oxo-oxazolidin-5-ylmethyl}-acetamide.
29) (S)-N-{3-[3-fluoro-4-(4-methoxymethoxy-piperidin-1-yl)-phenyl]-2-oxo-oxazolidin-5-ylmethyl}-acetamide,
30) (S)-N-{3-[4-(1,4-dioxa-8-aza-spiro[4.5]dec-8-yl)-3-fluoro-phenyl]-2-oxo-oxazolidin-5-ylmethyl}-acetamide,
31) (S)-N-{3-[3-fluoro-4-(4-methoxyimino-piperidin-1-yl)-phenyl]-2-oxo-oxazolidin-5-ylmethyl)-acetamide,
32) (S)-N-{3-[3-fluoro-4-(4-methoxycarbonylamino-piperidin-1-yl)-phenyl]-2-oxo-oxazolidin-5-ylmethyl}-acetamide,
33) (S)-N-{3-[3-fluoro-4-(4-methoxycarbonylhydrazono-piperidin-1-yl)-phenyl]-2-oxo-oxazolidin-5-ylmethyl}-acetamide,
34) (S)-N-(3-{3-fluoro-4-[4-(2-methyl-[1,3]dioxolan-2-ylmethyl)-piperidin-1-yl]-phenyl}-2-oxo-oxazolidin-5-ylmethyl)-acetamide,
35) (S)-N-(3-{3-fluoro-4-[4-(2-oxo-propyl)-piperidin-1-yl]-phenyl}-2-oxo-oxazolidin-5-ylmethyl)-acetamide,
36) (S)-8-{4-[5-(acetylamino-methyl)-2-oxo-oxazolidin-3-yl]-2-fluoro-phenyl}-1,4-dioxa-8-aza-spiro[4.5]decane-6-carboxylic acid methyl ester,
37) (S)-1-{4-[5-(acetylamino-methyl)-2-oxo-oxazolidin-3-yl]-2-fluoro-phenyl}-4-oxo-piperidin-3-carboxylic acid methyl ester,
38) (S)-N-{3-[3-fluoro-4-(4-oxo-4H-pyridin-1-yl)-phenyl]-2-oxo-oxazolidin-5-ylmethyl}-acetamide,
39) (S)-N-(3-{3-fluoro-4-[4-(2-methyl-[1,3]dioxolan-2-yl)-piperidin-1-yl]-phenyl}-2-oxo-oxazolidin-5-ylmethyl)-acetamide, 40) (S)-N-{3-[4-(4-acetyl-piperidin-1-yl)-3-fluoro-phenyl]-2-oxo-oxazolidin-5-ylmethyl}-acetamide,
41) (S)-N-{3-[3-fluoro-4-(3-hydroxymethyl-4-oxo-piperidin-1-yl)-phenyl]-2-oxo-oxazolidin-5-ylmethyl}-acetamide,
42) (S)-N-{3-[3-fluoro-4-(4-methoxycarbonyloxyimino-piperidin-1-yl)-phenyl]-2-oxo-oxazolidin-5-ylmethyl}-acetamide,
43) (S)-N-{3-[3-fluoro-4-(4-semicarbazono-piperidin-1-yl)-phenyl]-2-oxo-oxazolidin-5-ylmethyl}-acetamide,
44) (S)-N-(3-{3-fluoro-4-[4-(morpholin-4-ylimino)-piperidin-1-yl]-phenyl}-2-oxo-oxazolidin-5-ylmethyl)-acetamide,
45) (S)-N-[3-(3-fluoro-4-{4-[(2-hydroxy-ethyl)-hydrazono]-piperidin-1-yl}-phenyl)-2-oxo-oxazolidin-5-ylmethyl]-acetamide,
46) (S)-N-{3-[3-fluoro-4-(4-amidinohydrazono-piperidin-1-yl)-phenyl]-2-oxo-oxazolidin-5-ylmethyl}-acetamide,
47) (S)-N-{3-[3-fluoro-4-(4-acetoxyacetoxyimino-piperidin-1-yl)-phenyl]-2-oxo-oxazolidin-5-ylmethyl}-acetamide,
48) (S)-N-(3-{3-fluoro-4-[4-(2-hydroxymethyl-[1,3]dioxolan-2-yl)-piperidin-1-yl]-phenyl}-2-oxo-oxazolidin-5-ylmethyl)-acetamide,
49) (S)-N-{3-[3-fluoro-4-(4-benzyloxyacetoxyimino-piperidin-1-yl)-phenyl]-2-oxo-oxazolidin-5-ylmethyl}-acetamide,
50) (S)-N-{3-[3-fluoro-4-(4-hydrazono-piperidin-1-yl)-phenyl]-2-oxo-oxazolidin-5-ylmethyl}-acetamide,
51) (S)-(1-{4-[5-(acetylamino-methyl)-2-oxo-oxazolidin-3-yl]-2-fluoro-phenyl}-piperidin-4-ylideneaminooxy)-acetic acid methyl ester,
52) (S)-N-(3-{3-fluoro-4-[4-(2-hydroxy-ethoxyimino)-piperidin-1-yl]-phenyl}-2-oxo-oxazolidin-5-ylmethyl)-acetamide,
53) (S)-N-[3-(3-fluoro-4-{4-[4-(2-hydroxy-ethyl)-piperazin-1-ylimino]-piperidin-1-yl}-phenyl)-2-oxo-oxazolidin-5-ylmethyl]-acetamide,
54) (S)-N-[3-(3-fluoro-4-{4-[(2-hydroxy-acetyl)-hydrazono]-piperidin-1-yl}-phenyl)-2-oxo-oxazolidin-5-ylmethyl]-acetamide,
55) (S)-N-(3-{3-fluoro-4-[4-([1,2,4]triazol-4-ylimino)-piperidin-1-yl]-phenyl}-2-oxo-oxazolidin-5-ylmethyl)-acetamide,
56) (S)-N-{3-[3-fluoro-4-(2-hydroxymethyl-1,4-dioxa-8-aza-spiro[4.5]dec-8-yl)-phenyl]-2-oxo-oxazolidin-5-ylmethyl}-acetamide,
57) (S)-N-(3-{3-fluoro-4-[4-(2-methoxymethoxy-ethoxyimino)-piperidin-1-yl]-phenyl}-2-oxo-oxazolidin-5-ylmethyl)-acetamide,
58) (S)-N-(3-{3-fluoro-4-[4-(2-hydroxy-acetyl)-1-oxa-4,8-diaza-spiro[4.5]dec-8-yl]-phenyl}-2-oxo-oxazolidin-5-ylmethyl)-acetamide,
59) (S)-N-{3-[4-(4-cyanoimino-piperidin-1-yl)-3-fluoro-phenyl]-2-oxo-oxazolidin-5-ylmethyl}-acetamide,
60) (S)-(1-{4-[5-(acetylamino-methyl)-2-oxo-oxazolidin-3-yl]-2-fluoro-phenyl}-piperidin-4-ylidenehydrazinocarbonyl)-acetic acid ethyl ester,
61) (S)-N-(3-{3-fluoro-4-[2-(methoxymethoxy-methyl)-1,4-dioxa-8-aza-spiro[4.5]dec-8-yl]-phenyl}-2-oxo-oxazolidin-5-ylmethyl)-acetamide,
62) (S)-N-{3-[4-(4-allyloxyimino-piperidin-1-yl)-3-fluoro-phenyl]-2-oxo-oxazolidin-5-ylmethyl}-acetamide,
63) (S)-N-{3-[3-fluoro-4-(4-methoxyamino-piperidin-1-yl)-phenyl]-2-oxo-oxazolidin-5-ylmethyl}-acetamide,
64) (S)-N-{3-[3-fluoro-4-(4-methoxymethoxyimino-piperidin-1-yl)-phenyl]-2-oxo-oxazolidin-5-ylmethyl}-acetamide,
65) toluene-4-sulfonic acid (S)-1-{4-[5-(acetylamino-methyl)-2-oxo-oxazolidin-3-yl]-2-fluoro-phenyl}-piperidin-4-yl ester,
66) (S)-N-(3-{4-[4-(2,3-dihydroxy-propoxyimino)-piperidin-1-yl]-3-fluoro-phenyl}-2-oxo-oxazolidin-5-ylmethyl)-acetamide,
67) (S)-N-(3-{3-fluoro-4-[4-(thiazol-2-ylamino)-piperidin-1-yl]-phenyl}-2-oxo-oxazolidin-5-ylmethyl)-acetamide,
68) (S)-N-(3-{3-fluoro-4-[4-(2-methoxy-ethylamino)-piperidin-1-yl]-phenyl}-2-oxo-oxazolidin-5-ylmethyl)-acetamide,
69) (S)-N-(3-{4-[4-(acetoxy-methoxy-carbonylamino)-piperidin-1-yl]-3-fluorophenyl}-2-oxo-oxazolidin-5-ylmethyl)-acetamide,
70) (S)-N-{3-[3-fluoro-4-(4-methylamino-piperidin-1-yl)-phenyl]-2-oxo-oxazolidin-5-ylmethyl}-acetamide,
71) (S)-N-{3-[4-(4-dimethylamino-piperidin-1-yl)-3-fluoro-phenyl]-2-oxo-oxazolidin-5-ylmethyl}-acetamide,
72) (S)-N-{3-[4-(4-dimethylaminomethyleneamino-piperidin-1-yl)-3-fluorophenyl]-2-oxo-oxazolidin-5-ylmethyl}-acetamide,
73) (S)-2-fluoro-N-{3-[3-fluoro-4-(4-oxo-piperidin-1-yl)-phenyl]-2-oxo-oxazolidin-5-ylmethyl}-acetamide and
74) (S)-N-{3-[3-fluoro-4-(4-morpholin-4-yl-piperidin-1-yl)-phenyl]-2-oxo-oxazolidin-5-ylmethyl}-acetamide.

The compounds represented by the general formula (I) can be prepared by the method of reaction scheme 1. The method of synthesis is described below as regards substituted piperidines which are compounds of the general formula (I) where n=0. It should however be noted that substituted azepans where n=1 can also be synthesized by similar methods.

SCHEME 1

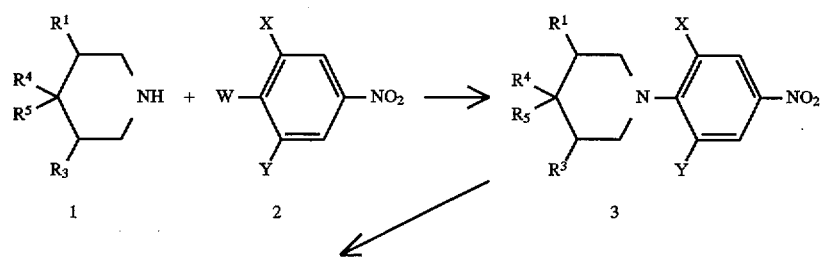

-continued
SCHEME 1

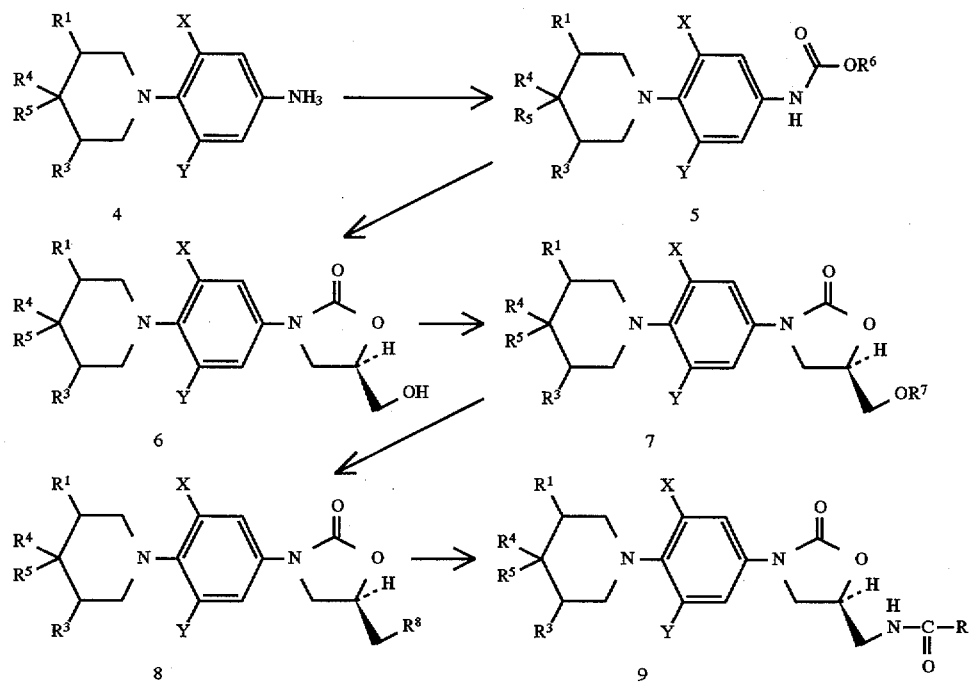

As shown, substituted piperidine of structure 1 or 4-hydroxypyridine is reacted with nitrobenzene 2 (Y=halogen or trifluoromethanesulfonate) in the presence of a suitable base such as N,N-diisopropylethylamine, sodium hydride or disodium hydrogenphosphate, and in a suitable solvent such as acetonitrile, tetrahydrofuran (THF), ethyl acetate, dimethyl sulfoxide (DMSO) or dimethyl formamide (DMF) at room temperature or reflux temperature to provide the adduct 3. When necessary, the side chains of $R^1$, $R^3$, $R^4$ and $R^5$ may be protected with a suitable protecting group(s) such as a benzyl or others that are described in Greene, T. W.; Wuts, P. G. M. "Protective Groups in Organic Synthesis", 2nd ed.,; John Wiley & Sons: New York (1991), the protecting groups being optionally removed after the synthesis. The nitro group of structure 3 is then reduced by hydrogenation in the presence of a suitable catalyst such as palladium on carbon or Lindlar catalyst in a suitable solvent such as ethyl acetate, THF, methanol, methylene chloride, chloroform or a mixture thereof (hydrogen is supplied in the form of a gas or indirectly via ammonium formate). The aniline 4 is then converted to its benzyl ($R^6=CH_2Ph$) or methyl ($R^6=CH_3$) urethane derivative 5, employing standard Schotten-Baumann conditions or other means known to one skilled in the art. The urethane 5 is then deprotenated by the action of a suitable base such as n-butyllithium or lithium bis(trimethylsilyl)amide in a suitable solvent such as THF or DMF at a suitable temperature in the range −78° to −40° C. to give a lithiated intermediate which is then treated with commercially available (−)-(R)-glycidyl butyrate. Warming to ambient temperature affords the compound 6 which is the enantiomer of hydroxymethyl-substituted oxazolidinone. Compound 6 is then converted to the corresponding mesylate ($R^7$=methanesulfonyl) or aryl sulfonate ($R^7=ArSO_2$, for example p-toluenesulfonyl) by reaction with, for example, methanesulfonyl chloride/pyridine or methanesulfonyl chloride/triethylamine/dichloromethane or methanesulfonyl chloride/triethylamine/DMSO or p-toluenesulfonyl chloride/pyridine. The resultant sulfonate derivative 7 is then reacted with sodium azide or potassium azide or the like in a solvent such as DMF or 1-methyl-2-pyrrolidinone optionally in the presence of a catalyst such as 18-crown-6 at a temperature of 50°–90° C. to afford the azide 8 ($R^8=N_3$). The azide is then reduced by hydrogenation with palladium on carbon, Lindlar catalyst or a platinum catalyst in an appropriate solvent such as ethyl acetate, methanol, methylene chloride, chloroform or a mixture thereof to give the corresponding amine 8 ($R^8=NH_2$). Alternatively, the azide can be reduced by reaction with a trivalent phosphorus compound such as triphenylphosphine in a suitable solvent such as THF followed by the addition of water. Alternatively, the mesylate or aryl sulfonate can be displaced with potassium phthalimide by refluxing in acetonitrile or other suitable solvent. The phthalimide 8 ($R^8$=phthalimide) is then deprotected by the addition of aqueous methyl amine in refluxing ethanol, to give the amine 8 ($R^8=NH_2$). The amine 8 is then acylated by methods known to those skilled in the art to give oxazolidinones of structure 9. For example, the amine can be reacted with an acid chloride or anhydride in a basic solvent such as pyridine at a temperature ranging from −30° to 30° C. to provide the acylated compound 9 (R=optionally substituted alkyl). A substituent such as amino, hydroxy, ester or carbonyl group in $R^4$ or $R^5$ can be converted to the corresponding derivative such as alkylamide, ether, carboxyl, hydroxyalkyl or oxime group by methods known to those skilled in the art. It will be apparent to one skilled in the art that other acyl groups within the scope of this invention can be readily appended to the amine 8 ($R^6=NH_2$) by standard acylation techniques, for example, those highlighted in March, J. "Advanced Organic Chemistry", 3rd ed.; John Wiley & Sons: New York, 1985; p 370–375, to give additional examples of compound 9. Any appended protecting group on the side chains of $R^1$, $R^3$, $R^4$ and $R^5$ on the piperidine ring can be removed employing appropriate conditions such as those noted in Greene, T. W.; Wuts, P. G. M., "Protective Groups in Organic Synthesis," 2nd ed.; John Wiley & Sons: New York (1991). The compounds of structure 9 represent examples of piperidine-substituted oxazolidinone antimicrobial agents of Formula (I), which are the subject of this invention.

These compounds are useful for the treatment of microbial infections in humans and other warm blooded animals by either parenteral, oral, or topical administration.

The pharmaceutical compositions of this invention may be prepared by combining the compounds of Formula (I) of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing conventional coloring agents, flavoring agents, stabilizers and thickening agents.

Preferably, the pharmaceutical composition is provided employing conventional techniques in unit dosage form containing effective or appropriate amounts of the active component, that is, the compound of Formula (I) according to this invention.

The quantity of active component, that is the compound of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating, or combatting bacterial infections in humans and other animals that have been diagnosed with bacterial infections, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100 mg/kg, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula (I) according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula (I) as a soluble salt (acid addition salt or base salt) dissolved in a pharmaceutically acceptable liquid carrier such as, for example, water-for-injection and a suitably buffered isotenic solution, for example, having a pH of about 3.5–6. Suitable buffering agents include, for example, trisodium orthophosphate, sodium bicarbonate, sodium citrate, N-methylglucamine, L(+)-lysine and L(+)-arginine, to name a few. The compound according to Formula (I) generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned antibacterially effective amount of dosage. The compounds of Formula (I) according to this invention are advantageously administered orally in solid and liquid dosage forms.

As a topical treatment, an effective amount of Formula (I) is admixed in a pharmaceutically acceptable gel or cream vehicle that can be applied to the patient's skin at the area of treatment. Preparation of such creams and gels is well known in the art and can include penetration enhancers.

The compounds of this invention are useful antimicrobial agents, effective against various human and veterinary pathogens, including multiply-resistant staphylococci and streptococci, as well as anaerobic organisms such as bacteroides and clostridia species, and acid-resistant organisms such as *Mycobacterium tuberculosis* and *Mycobacterium avium*.

We now describe the test method for verifying the antimicrobial action of compounds within the scope of this invention. Compounds of this invention were subjected to various antimicrobial activity tests, in which they exhibited antimicrobial activity against multiply-resistant staphylococci and streptococci, as well as anaerobic organisms such as bacteroides and clostridia species, and acid-resistant organisms such as *Mycobacterium tuberculosis* and *Mycobacterium avium*. MIC (minimum inhibitory concentration) data for compounds of this invention against typical organisms were determined by the MIC test method to be described below and the results are shown in Table 1. The antimicrobial action of compounds of this invention was also verified by the Murine Assay procedure (in vivo) to be described below. Compounds with numbers 7, 11, 30 and 31 had $ED_{50}$ values of 8.1 mg/kg, 8.2 mg/kg, 2.8 mg/kg and 5.0 mg/kg, respectively, upon oral administration; hence, they were as effective as the control Vancomycin.

MIC Test Method

The in vitro MICs of test compounds were determined by a standard agar dilution method. A stock drug solution of each analog is prepared in the preferred solvent, usually $DMSO:H_2O$ (1:3). Serial 2-fold dilutions of each sample are made using 1.0 ml aliquots of sterile distilled water. To each 1.0 ml aliquot of drug is added 9 ml of molten Mueller Hinton agar medium. The drug-supplemented agar is mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35° C.

Following incubation the Minimum Inhibitory Concentration (MIC μg/ml), the lowest concentration of drug that inhibits visible growth of the organism, is read and recorded. Vancomycin is included in the assay and serves as a comparator and quality control compound. The result for the control compound against each test strain is compared to previous and/or published MIC results as a means of validating the test.

TABLE 1

Minimum Inhibitory Concentrations (MIC, μg/ml)

| Compound No. | S. aureus | S. epidermidis | S. pyogenes | M. tuberculosis |
|---|---|---|---|---|
| 1 | 8* | 2 | 2 | 1 |
| 2 | 8* | 1 | 4 | — |
| 3 | 8 | 2 | 2 | 1 |
| 4 | 8 | 2 | 2 | — |
| 6 | >64 | 32 | 1 | — |
| 7 | 2 | 0.5 | 2 | — |
| 9 | 16 | 2 | 4 | — |
| 10 | 16 | 2 | 2 | — |
| 11 | 2 | 1 | 1 | — |
| 29 | 8 | 2 | 8 | — |
| 30 | 8 | 2 | 4 | — |
| 31 | 4 | 1 | 4 | — |
| 32 | 4 | 2 | 2 | — |
| 33 | 2 | 0.5 | 1 | — |
| 34 | 16 | 4 | 4 | — |
| 35 | 8 | 2 | 2 | — |
| 36 | 16 | 4 | 4 | — |
| 37 | 16 | 4 | 4 | — |
| 38 | 16 | 2 | 0.5 | — |
| 39 | 8 | 2 | 2 | — |
| 40 | 4 | 1 | 2 | — |
| 41 | 8 | 2 | 2 | — |
| 42 | 2 | 0.5 | 1 | — |
| 43 | 2 | 0.5 | 2 | — |
| 44 | 4 | 0.5 | 2 | — |
| 45 | 4 | 0.5 | 1 | — |
| 46 | 8 | 2 | 0.5 | — |
| 47 | 4 | 0.5 | 1 | — |
| 48 | 16 | 2 | 24 | — |
| 49 | 2 | 0.5 | 2 | — |
| 50 | 2 | 0.5 | 2 | — |
| 51 | 8 | 1 | 2 | — |
| 52 | 8 | 1 | 2 | — |
| 53 | 4 | 0.5 | 1 | — |
| 54 | 16 | 4 | 4 | — |
| 55 | 4 | 1 | 2 | — |
| 56 | 16 | 2 | 4 | — |
| 57 | 16 | 2 | 4 | — |
| 58 | 16 | 4 | 4 | — |
| 60 | 4 | 1 | 2 | — |
| 61 | 16 | 4 | 8 | — |
| 62 | 8 | 1 | 2 | — |
| 63 | 4 | 2 | 4 | — |
| 64 | 8 | 2 | 2 | — |
| 65 | 8 | 4 | 8 | — |
| 66 | 8 | 1 | 2 | — |
| 67 | 16 | 2 | 2 | — |
| 68 | 32 | 2 | 1 | — |
| 69 | 8 | 1 | 0.5 | — |
| 71 | 32 | 2 | 1 | — |
| Vancomycin | 1 | 2 | 0.5 | — |

S. aureus: Staphylococcus aureus (UC 9213, *: UC 9218)
S. epidermidis: Staphylococcus epidermidis (UC 12084)
S. pyogenos: Streptococcus pyogenes (UC 152)
M. tuberculosis: Mycobacterium tuberculosis Murine Assay Procedure Groups of female mice (six mice of 18–20 grams each) were injected intraperitoneally with *Staphylococcus aureus* (UC 9213) bacteria which were thawed just prior to use and suspended in brain heart infusion with 4% brewer's yeast (*Staphylococcus aureus*) or brain heart infusion (Streptococcus species). Antibiotic treatment at six dose levels per drug (compound) was administered one hour and five hours after infection by either oral intubation or subcutaneous routes. Survival was observed daily for six days. $ED_{50}$ values based on mortality ratios were calculated using probit analysis. The subject compounds were compared against vancomycin as a control.

It should be noted here that none of the compounds of this invention, nor pharmaceutically acceptable salts thereof have been found to have toxicity that would cause any problem.

DESCRIPTION OF THE PREFERRED EMBODIMENTS

The following examples are provided to further illustrate this invention but they should not be taken as limiting.

EXAMPLE 1

Preparation of (S)-N-[3-(3-fluoro-4-piperidin-1-yl-phenyl)-2-oxo-oxazolidin-5-ylmethyl]-acetamide (Compound No. 2)

Diisopropylethylamine (15.7 ml) and 3,4-difluoronitrobenzene (5.0 ml) were added successively to an ethyl acetate solution (70 ml) of piperidine (5.77 g) and the mixture was stirred at room temperature for 2 days. Water was added to the reaction solution and the separating ethyl acetate layer was washed with water and brine, dried over anhydrous sodium sulfate. The solvent was evaporated to afford a nitro compound (10.1 g) in a yield of 100%. Palladium on carbon (10%, 1.0 g) was added to an ethyl acetate solution (101 ml) of the nitro compound (10.1 g) and the mixture was stirred at room temperature for 14 h under hydrogen atmosphere. The palladium on carbon was filtered off and the filtrate was concentrated under vacuum to yield an amine (8.75 g, 100%). Sodium hydrogencarbonate (5.0 g) and benzyloxycarbonyl chloride (8.4 ml) were added successively to a tetrahydrofuran (THF) solution (100 ml) of the amine (8.75 g), and the mixture was stirred at room temperature for 14 h. Water was added to the reaction solution and the separating THF layer was washed with water and brine, dried over anhydrous sodium sulfate. The solvent was evaporated and the residue was purified by silica gel column chromatography (solvent: ethyl acetate/hexane/chloroform= 1/6/4) to afford a benzyl carbamate (14.5 g) in a yield of 98%. Butyl lithium (1.6M hexane solution: 5.2 ml) was added to a THF solution (24 ml) of the benzyl carbamate (2.75 g) at −78° C. and the mixture was stirred for 5 min. At the same temperature, (R)-(−)-glycidyl butyrate (1.25 ml) was added to the stirred solution and the mixture was stirred for 14 h while the temperature was raised slowly to room temperature. Water was added to the reaction solution and the separating THF layer was washed with water and brine, dried over anhydrous sodium sulfate. The solvent was evaporated and the residue was purified by silica gel column chromatography (solvent: ethyl acetate/hexane=3/1) to afford an alcohol (2.20 g) in a yield of 89%. Tosyl chloride (2.85 g) was added to a pyridine solution (8 ml) of the alcohol (2.20 g) and the mixture was stirred at room temperature for 6 h. Water (32 ml) was added to the reaction solution and the mixture was stirred for 1 h. The resulting precipitate was collected by filtration and washed with water, followed by drying under vacuum at room temperature to afford a tosylate (3.28 g) in a yield of 98%. Sodium azide (3.80 g) was added to a dimethylformamide (DMF)

solution (23 ml) of the tosylate (3.28 g) at room temperature and the mixture was stirred at 65° C. for 5.5 h. After the reaction mixture was cooled to room temperature, water was added and the mixture was extracted with ethyl acetate; the organic layer was concentrated under vacuum. The resulting residue was dissolved in ethyl acetate and washed with water and brine, dried over anhydrous sodium sulfate. The solvent was evaporated and the residue was purified by silica gel column chromatography (solvent: ethyl acetate/hexane= 1/1) to afford an azide (2.20 g) in a yield of 94%. Acetic anhydride (0.65 ml) and pyridine (1.0 ml) were added to an ethyl acetate solution (19 ml) of the azide (2.20 g) at room temperature; after addition of palladium on carbon (10%, 0.22 g), the mixture was stirred at room temperature for 6 h under 1 atm hydrogen atmosphere. The palladium on carbon was filtered off and the filtrate was washed with water and brine, dried over anhydrous sodium sulfate. The solvent was evaporated and the residue was purified by silica gel column chromatography (solvent: acetone/hexane=1/1) to afford the title compound (1.47 g) in a yield of 64%.

EXAMPLE 2

Preparation of (S)-N-{3-[3-fluoro-4-(4-hydroxymethyl-piperidin-1-yl)-phenyl]-2-oxo-oxazolidin-5-ylmethyl)-acetamide
(Compound No. 4)

Using a commercially available piperidine-4-carboxylic acid ethyl ester, (S)-1-{4-[5-(acetylamino-methyl)-2-oxo-oxazolidin-3-yl]-2-fluoro-phenyl}-piperidine-4-carboxylic acid ethyl ester (Compound No. 1) was synthesized by the same method as in Example 1. To a THF solution (6.6 ml) of this compound (661 mg), lithium chloride (275 mg), sodium borohydride (245 mg) and ethanol (4.5 ml) were added successively and the mixture was stirred at room temperature for 14 h. A saturated aqueous ammonium chloride solution was added to the reaction solution and the reaction mixture was extracted with methylene chloride; the organic layer was washed with water and brine, dried over anhydrous sodium sulfate. The solvent was evaporated and the residue was purified by silica gel column chromatography (solvent: chloroform/methanol=25/1–15/1) to afford the title compound (402 mg) in a yield of 68%.

EXAMPLE 3

Preparation of (S)-N-3-[3-fluoro-4-(4-oxo-piperidin-1-yl)-phenyl]-2-oxo-oxazolidin-5-ylmethyl}-acetamide (Compound No. 7)

Using a commercially available 1,4-dioxo-8-aza-spiro[4.5]decane, (S)-N-3-[4-(1,4-dioxa-8-aza-spiro[4.5]dec-8-yl)-3-fluoro-phenyl]-2-oxo-oxazolidin-5-ylmethyl}-acetamide (Compound No. 30) was synthesized by the same method as in Example 1. To an acetone solution (70 ml) of this compound (3.79 g), water (20 ml) and p-toluenesulfonic acid monohydrate (3.66 g) were added successively and the mixture was heated under reflux for 3 h. After the reaction mixture was cooled to room temperature, acetone was distilled off and the aqueous layer was neutralized with triethylamine. The solution was extracted with methylene chloride and the organic layer was washed with brine, dried over anhydrous sodium sulfate. The solvent was evaporated and the residue was purified by silica gel column chromatography (solvent: chloroform/methanol=50/1–25/1) to afford the title compound (3.05 g) in a yield of 91%.

EXAMPLE 4

Preparation of (S)-N-{3-[4-(4-amino-piperidin-1-yl)-3-fluoro-phenyl]-2-oxo-oxazolidin-5-ylmethyl}-acetamide (Compound No. 6)

Sodium carbonate (18.1 g) and benzyl bromide (10.0 ml) were added successively to an acetonitrile solution (80 ml) of (4-amino-piperidin-1-yl)-acetic acid ethyl ester (4.89 g) and the mixture was stirred at room temperature for 14 h. The reaction solution was filtered and the filtrate was concentrated under vacuum. The residue was dissolved in methylene chloride and washed with water and brine, dried over anhydrous sodium sulfate. The solvent was evaporated and the residue was purified by silica gel column chromatography (solvent: ethyl acetate/hexane=1/6) to afford a dibenzyl compound (8.24 g) in a yield of 82%. Potassium hydroxide (34 g) was added to an ethylene glycol solution (170 ml) of the dibenzyl compound (8.24 g) and the mixture was stirred for 15 min. Thereafter, hydrazine monohydrate (5.7 ml) was added and the mixture was heated under reflux for 2 h. After the reaction mixture was cooled to room temperature, water was added to the reaction solution and the precipitating crystal was collected by filtration and washed with water, followed by drying under vacuum at room temperature to afford dibenzyl-piperidin-4-yl-amine (6.43 g) in a yield of 98%.

Using the amino compound, (S)-N-{3-[4-(4-dibenzylamino-piperidin-1-yl)-3-fluoro-phenyl]-2-oxo-oxazolidin-5-ylmethyl}-acetamide (Compound No. 5) was synthesized by the same method as in Example 1. To a methanol solution (200 ml) of this compound (5.28 g), palladium hydroxide on carbon (20%, 3.3 g) was added and the mixture was stirred at room temperature under 3 atm hydrogen atmosphere. Palladium hydroxide on carbon was filtered off and the filtrate was concentrated under vacuum to afford the title compound (3.48 g) in a yield of 100%.

EXAMPLE 5

Preparation of (S)-N-{3-[3-fluoro-4-(4-hydroxyimino-piperidin-1-yl)-phenyl]-2-oxo-oxazolidin-5-ylmethyl}-acetamide
(Compound No. 11)

Sodium acetate (517 mg) and hydroxylamine hydrochloride (219 mg) were successively added to a methanol-methylene chloride solution (10-10 ml) of 1.00 g of the (S)-N-{3-[3-fluoro-4-(4-oxo-piperidin-1-yl)-phenyl]-2-oxo-oxazolidin-5-ylmethyl}-acetamide (Compound No. 7) synthesized in Example 3, and the mixture was stirred at room temperature for 2 days. The solvent was evaporated and the residue was dissolved in methanol, followed by addition of a silica gel (8 g). Methanol was evaporated and the residue was purified by silica gel column chromatography (solvent: chloroform/methanol=50/1–25/1) to afford the title compound (852 mg) in a yield of 82%.

EXAMPLE 6

Preparation of (S)-N-{3-[3-fluoro-4-(4-methoxycarbonylhydrazono-piperidin-1-yl)-phenyl]-2-oxo-oxazolidin-5-ylmethyl}-acetamide
(Compound No. 33)

Methyl carbazinate (135 mg) was added to a methanol-methylene chloride solution (5–4 ml) of 500 mg of the (S)-N-{3-[3-fluoro-4-(4-oxo-piperidin-1-yl)-phenyl]-2-oxo-oxazolidin-5-ylmethyl)-acetamide (Compound No. 7) synthesized in Example 3, and the mixture was stirred at room temperature for 14 h. The solvent was evaporated and the residue was purified by silica gel column chromatography (solvent: chloroform/methanol=50/1) to afford the title compound (487 mg) in a yield of 81%.

EXAMPLE 7

Preparation of (S)-N-(3-3-fluoro-4-[4-(2-methyl-[1,3]dioxolan-2-ylmethyl)-piperidin-1-yl]-phenyl}-2-oxo-oxazolidin-5-ylmethyl)-acetamide
(Compound No. 34)

Dimethyl(2-oxopropyl)phosphate (2.85 ml) and N-benzyl-4-piperidone (3.00 g) were successively added to an ethanol solution (14 ml) of potassium hydroxide (0.93 g) and the mixture was stirred at room temperature for 14 h. Water was added to the reaction solution and the mixture was extracted with ether, washed with water and brine, and dried over anhydrous sodium sulfate. The solvent was evaporated and the residue was purified by ODS-silica gel column chromatography (solvent: methanol/water=2/1–4/1) to afford an enone (2.07 g) in a yield of 57%. To a benzene solution (50 ml) of the enone (3.69 g), ethylene glycol (4.49 ml) and p-toluenesulfonic acid monohydrate (3.37 g) were added successively and the mixture was refluxed for 5 h under heating with a Dean-Stark apparatus. After the reaction mixture was cooled to room temperature, a saturated aqueous sodium carbonate solution was added and the mixture was extracted with ethyl acetate, washed with water and brine, and dried over anhydrous sodium sulfate. The solvent was evaporated to afford a ketal benzyl compound (4.20 g) in a yield of 95%. To a methanol solution (42 ml) of the ketal benzyl compound (4.20 g), palladium hydroxide on carbon (0.42 g) was added and the mixture was stirred for 2 days under 3 atm hydrogen atmosphere. The palladium hydroxide on carbon was filtered off and the filtrate was concentrated under vacuum to afford a ketal compound (2.80 g) in a yield of 98%. Using this compound, the procedure of Example 1 was repeated to afford the title compound.

EXAMPLE 8

Preparation of (S)-8-{4-[5-acetylamino-methyl)-2-oxo-oxazolidin-3-yl]-2-fluorophenyl}-1,4-dioxa-8-aza-spiro[4.5]decane-6-carboxylic acid methyl ester (Compound No. 36)

Diisopropylethylamine (7.71 ml), then benzyloxycarbonyl chloride (3.0 ml) were added to a dichloromethane solution (40 ml) of 3-carbomethoxy-4-piperidone hydrochloride (3.43 g) at 0° C. and the mixture was stirred at room temperature for 14 h. The solvent was evaporated and the residue was purified by silica gel column chromatography (solvent: hexane/ethyl acetate=7/3) to afford an N-benzyl carbamate (4.57 g) in a yield of 79%. The benzyl carbamate, p-toluenesulfonic acid hydrate (2.45 g) and ethylene glycol (8.69 g) were added to benzene (100 ml) and the mixture was refluxed for 6 h under heating with water being removed continuously with a water separator. After being cooled to room temperature, the reaction solution was washed first with a saturated aqueous sodium hydrogencarbonate, then with water; the organic layer was dried and concentrated under vacuum to afford an ethyleneketal benzyl carbamate (4.89 g) in a yield of 94%. This compound was dissolved in a mixed solvent consisting of dichloromethane (20 ml) and methanol (50 ml). To the solution, palladium hydroxide on carbon (20%, 500 mg) was added and the mixture was stirred at room temperature for 14 h under 3 atm hydrogen atmosphere. The palladium hydroxide on carbon was filtered off and the filtrate was concentrated under vacuum to afford an ethyleneketal compound (3.44 g) in a yield of 100%. Using this compound, the procedure of Example 1 was repeated to afford the title compound.

EXAMPLE 9

Preparation of (S)-1-{4-[5-(acetylamino-methyl)-2-oxo-oxazolidin-3-yl]-2-fluorophenyl}-4-oxo-piperidin-3-carboxylic acid methyl ester (Compound No. 37)

Using 400 mg of the (S)-8-{4-[5-(acetylamino-methyl)-2-oxo-oxazolidin-3-yl]-2-fluoro-phenyl}-1,4-dioxa-8-aza-spiro[4.5]decane-6-carboxylic acid methyl ester (Compound No. 36) synthesized in Example 8, the procedure of Example 3 was repeated to afford the title compound (49 mg).

EXAMPLE 10

Preparation of (S)-N-{3-[3-fluoro-4-(4-oxo-4H-pyridin-1-yl)-phenyl]-2-oxo-oxazolidin-5-ylmethyl}-acetamide (Compound No. 38)

Sodium hydride (1.88 g) was added to an anhydrous dimethylformamide (DMF) solution (50 ml) of 4-hydroxypyridine (3.28 g) at 0° C. and the mixture was stirred for 30 min. Subsequently, 3,4-difluoronitrobenzene (5.0 g) was added at the same temperature and the mixture was stirred at room temperature for 14 h. Water was added to the reaction solution and the solvent was evaporated. Toluene was added and water was removed by azeotropy and the residue was suspended in dichloromethane (100 ml). The insolubles were rejected by filtration through Celite and the filtrate was concentrated under vacuum. The residue was purified by silica gel column chromatography (solvent: methanol/dichloromethane=5/95) to afford a nitro compound (4.89 g) in a yield of 66%. The nitro compound was reduced catalytically with a Lindlar catalyst and subsequently treated with benzyloxycarbonyl chloride to afford a benzyl carbamate (1.71 g) in a yield of 24%. Lithium bis(trimethylsilyl)amide (1M THF solution; 4.0 ml) was added to a DMF solution (20 ml) of the benzyl carbamate (1.22 g) at −78° C. and the mixture was stirred for 5 min. At the same temperature, (R)-(−)-glycidyl butyrate (0.56 ml) was added to the stirred solution and the mixture was stirred for 14 h while the temperature was raised slowly to room temperature, with the stirring being continued for three more days at room temperature. Water was added to the reaction solution and the solvent was evaporated. A dichloromethane-soluble portion was produced by dehydration and desalting in accordance with the same procedure as described above and purified by silica gel column chromatography (solvent: methanol/dichloromethane=7/93) to afford an alcohol (745 mg). Triethylamine (0.4 ml), then methanesulfonyl chloride (0.2 ml) were added to a dimethyl sulfoxide solution (10 ml) of the alcohol (540 mg) at 0° C. and the mixture was stirred at room temperature for 18 h. The solvent was evaporated and the residue was dissolved in DMF (10 ml). Sodium azide (160 ml) was added to the solution at room temperature and the mixture was stirred at 65° C. for 14 h. After the reaction mixture was cooled to room temperature, the insolubles were filtered off and the filtrate was concentrated under vacuum. The resulting residue was purified by silica gel column chromatography (solvent: methanol/dichloromethane=5/95) to afford an azide (149 mg) in a yield of 26%. Triphenylphosphine (137 mg) was added to an anhydrous TFH solution (4 ml) of the azide at room temperature and the mixture was stirred for 2 h. Water (0.1 ml) was added to the reaction mixture, followed by stirring at 40° C. for 4 h, then at room temperature for 14 h. The solvent was evaporated and the residue was dehydrated by azeotropy with toluene. The resulting residue was suspended in dichloromethane (10 ml) and, after addition of pyridine (0.8 ml) and acetic anhydride (1.0 ml) at 0° C., the mixture was stirred at room temperature for 6 h. The solvent was evaporated and the residue was purified by silica gel column chromatography (solvent: methanol/dichloromethane=7/93) to afford the title compound (167 mg) in a yield of 100%.

EXAMPLE 11

Preparation of (S)-N-(3-{3-fluoro-4-[4-(2-methyl-[1,3]dioxolan-2-yl)-piperidin-1-yl]-phenyl}-2-oxo-oxazolidin-5-ylmethyl)-acetamide (Compound No. 39)

Potassium carbonate (5.27 g) and benzyl bromide (3.97 ml) were successively added to an acetonitrile solution (80 ml) of ethyl isonipecotate (5.00 g) and the mixture was stirred at room temperature for 14 h.

Water was added to the reaction solution and the mixture was extracted with ethyl acetate, washed with water and brine, and dried over anhydrous sodium sulfate. The solvent was evaporated and the residue was purified by silica gel column chromatography (solvent: ethyl acetate/hexane=1/2) to afford a benzyl compound (7.03 g) in a yield of 89%. A THF solution (25 ml) of the benzyl compound (5.00 g) was added dropwise to a THF solution (10 ml) of lithium diisopropylamide (1.5M cyclohexane solution; 17.5 ml) at −78° C. and the mixture was stirred for 15 min. At the same temperature, a THF solution (20 ml) of acetyl chloride (2.16 ml) was added dropwise and the mixture was stirred at −78° C. for 30 min and then for 14 h with the temperature raised to room temperature. A saturated aqueous sodium hydrogencarbonate solution was added to the reaction solution and the mixture was extracted with ethyl acetate, washed with water and brine, and dried over anhydrous sodium sulfate. The solvent was evaporated and the residue was purified by silica gel column chromatography (solvent: ethyl acetate/ hexane=1/2) to afford a crude acetyl-ester compound (5.05 g). A 10% aqueous sodium hydroxide solution (20 ml) was added to a THF solution (20 ml) of the crude acetyl-ester compound (5.05 g) and the mixture was stirred at 60° C. for 14 h. After the reaction mixture was cooled to room temperature, THF was evaporated and the resulting aqueous solution was adjusted to pH of 4 by addition of conc. hydrochloric acid and the mixture was stirred at 120° C. for 30 min. After being cooled to room temperature, the reaction mixture was neutralized with a saturated aqueous sodium hydrogencarbonate solution and extracted with ethyl acetate. The ethyl acetate layer was washed with water and brine, and dried over anhydrous sodium sulfate. The solvent was evaporated to afford an acetyl compound (2.15 g) in a yield of 49% (by a two-step process). Ethylene glycol (2.76 ml) and p-toluenesulfonic acid monohydrate (2.07 g) were successively added to a benzene solution (30 ml) of the acetyl compound (2.15 g) and the mixture was refluxed for 5 h by heating with a Dean-Stark apparatus. After the reaction mixture was cooled to room temperature, a saturated aqueous sodium carbonate solution was added and the mixture was extracted with ethyl acetate, washed with water and brine, and dried over anhydrous sodium sulfate. The solvent was evaporated to afford a ketal benzyl compound (2.59 g) in a yield of 100%.

Palladium hydroxide on carbon (0.26 g) was added to a methanol solution (26 ml) of the ketal benzyl compound (2.59 g) and the mixture was stirred for 2 h under 3 atm hydrogen atmosphere. The palladium hydroxide on carbon was filtered off and the filtrate was concentrated under vacuum to afford a ketal compound (1.69 g) in a yield of 100%. Using this ketal compound, the procedure of Example 1 was repeated to afford the title compound.

EXAMPLE 12

Preparation of (S)-N-{3-[3-fluoro-4-(3-hydroxymethyl-4-oxo-piperidin-1-yl)-phenyl]-2-oxo-oxazolidin-5-ylmethyl)-acetamide (Compound No. 41)

Using 600 mg of the (S)-8-{4-[5-(acetylamino-methyl)-2-oxo-oxazolidin-3-yl]-2-fluoro-phenyl}-1,4-dioxa-8-aza-spiro[4.5]decane-6-carboxylic acid methyl ester (Compound No. 36) synthesized in Example 8, reduction was performed by repeating the procedure of Example 2, thus affording an alcohol (361 mg) in a yield of 66%. Using 302 mg of the alcohol, the procedure of Example 3 was repeated to afford the title compound (155 mg) in a yield of 58%.

EXAMPLE 13

Preparation of (S)-N-(3-{3-fluoro-4-[4-(2-hydroxymethyl-[1,3]dioxolan-2-yl)-piperidin-1-yl]-phenyl}-2-oxo-oxazolidin-5-ylmethyl)-acetamide (Compound No. 48)

A ketal compound was synthesized by repeating the procedure of Example 11, except that the acetyl chloride as a feed material was replaced by benzyloxyacetyl chloride. Using this ketal, the procedure of Example 1 was repeated to synthesize a compound, from which the protective benzyl group was removed to afford the title compound.

EXAMPLE 14

Preparation of (S)-N-{3-[3-fluoro-4-(2-hydroxymethyl-1,4-dioxa-8-aza-spiro[4.5]dec-8-yl)-phenyl]-2-oxo-oxazolidin-5-ylmethyl}-acetamide (Compound No. 56)

Para-toluenesulfonic acid monohydrate (299 mg) and glycerol (0.21 ml) were added successively to a benzene suspension (10 ml) of 500 mg of the (S)-N-{3-[3-fluoro-4-(4-oxo-piperidin-1-yl)-phenyl]-2-oxo-oxazolidin-5-ylmethyl}-acetamide (Compound No. 7) which was synthesized in Example 3, and the mixture was heated under reflux for 4 h, with water being removed continuously by means of a water separator. After the reaction mixture was cooled to room temperature, a saturated aqueous sodium hydrogencarbonate solution was added and the mixture was stirred. Thereafter, the solution was extracted with methylene chloride and the organic layer was washed with water and brine and dried over anhydrous sodium sulfate. The solvent was evaporated under vacuum and the residue was purified by silica gel column chromatography (solvent: chloroform/ methanol=50/1–25/1) to afford the title compound (510 mg) in a yield of 84%.

EXAMPLE 15

Preparation of (S)-N-(3-{3-fluoro-4-[4-(2-hydroxy-acetyl)-1-oxa-4,8-diaza-spiro[4.5]dec-8-yl]-phenyl}-2-oxo-oxazolidin-5-ylmethyl)-acetamide (Compound No. 58)

Ethanolamine (0.31 ml) was added to a benzene suspension (10 ml) of 600 mg of the (S)-N-{3-[3-fluoro-4-(4-oxo-piperidin-1-yl)-phenyl]-2-oxo-oxazolidin-5-ylmethyl}-acetamide (Compound No. 7) which was synthesized in Example 3, and the mixture was heated under reflux for 2 h, with water being removed continuously by means of a water separator. After the reaction mixture was cooled to room temperature, the resulting crystal was collected by filtration, washed with benzene and dried under vacuum at room temperature to yield 671 mg of an oxazolidin compound. To a methylene chloride solution (5 ml) of the oxazolidin compound (671 mg), 0.17 ml of pyridine and 0.30 ml of benzyloxyacetyl chloride were added successively and the mixture was stirred at room temperature for 48 h. Following the addition of methanol, the mixture was stirred for 30 min and the solvent was evaporated. The residue was purified by silica gel column chromatography (solvent: chloroform/ methanol=50/1) to afford a benzyloxyacetyl compound (574 mg) in a yield of 62%. To a methanol-methylene chloride solution (8–4 ml) of the benzyloxyacetyl compound (574 mg), 57 mg of palladium on carbon was added and the mixture was stirred at room temperature for 14 h under 1 atm hydrogen atmosphere. After the catalyst was filtered off, the solvent was evaporated and the residue was purified by silica gel column chromatography (solvent: chloroform/methanol=50/1–25/1–10/1) to afford the title compound (148 mg) in a yield of 31%.

EXAMPLE 16

Preparation of (S)-N-{3-[3-fluoro-4-(4-methoxyamino-piperidin-1-yl)-phenyl]-2-oxo-oxazolidin-5-ylmethyl}-acetamide (Compound No. 63)

(S)-N-{3-[3-fluoro-4-(4-methoxyimino-piperidin-1-yl)-phenyl]-2-oxo-oxazolidin-5-ylmethyl}-acetamide (Compound No. 31) was synthesized using the (S)-N-{3-[3-fluoro-4-(4-oxo-piperidin-1-yl)-phenyl]-2-oxo-oxazolidin-5-ylmethyl}-acetamide (Compound No. 7) which was synthesized in Example 3. To a methanol solution (4 ml) of Compound No. 31 (594 mg), 0.69 ml of boran-pyridine complex (8M) was added at 0° C. and the mixture was stirred for 5 min. Thereafter, 8 ml of 10% HCl was added and the mixture was further stirred at room temperature for 15 min. After neutralization with sodium carbonate, the solution was extracted with methylene chloride and the organic layer was washed with water and brine and dried over anhydrous sodium sulfate. The solvent was evaporated under vacuum and the residue was purified by silica gel column chromatography (solvent: chloroform/methanol=50/1) to afford the title compound (399 mg) in a yield of 67%.

EXAMPLE 17

Preparation of (S)-N-(3-{4-[4-(2,3-dihydroxy-propoxyimino)-piperidin-1-yl]-3-fluoro-phenyl}-2-oxo-oxazolidin-5-ylmethyl)-acetamide (Compound No. 66)

(S)-N-{3-[4-(4-allyloxyimino-piperidin-1-yl)-3-fluoro-phenyl]-2-oxo-oxazolidin-5-ylmethyl}-acetamide (Compound No. 62) was synthesized using the (S)-N-{3-[3-fluoro-4-(4-oxo-piperidin-1-yl)-phenyl]-2-oxo-oxazolidin-5-ylmethyl}-acetamide (Compound No. 7) which was synthesized in Example 3. To an acetonitrile-water solution (20-2 ml) of Compound No. 62, (715 mg), 0.5 ml of osmium tetroxide (2.5 wt % tert-butanol solution) and 0.34 ml of N-methyl morpholine-N-oxide (60 wt % aq. sol.) were added successively and the mixture was stirred at room temperature for 5 h. A saturated aqueous sodium thiosulfate solution was added and the mixture was stirred for 30 min. The solution was extracted with methylene chloride-methanol and the organic layer was washed with water and brine and dried over anhydrous sodium sulfate. The solvent was evaporated under vacuum and the residue was purified by silica gel column chromatography (solvent: chloroform/methanol=25/1–10/1) to afford the title compound (582 mg) in a yield of 75%.

EXAMPLE 18

Preparation of (S)-N-{3-[3-fluoro-4-(4-methylamino-piperidin-1-yl)-phenyl]-2-oxo-oxazolidin-5-ylmethyl}-acetamide (Compound No. 70)

Methylamine hydrochloride (0.46 g) and palladium on carbon (0.20 g) were added to a methanol-methylene chloride solution (20-20 ml) of 2.00 g of the (S)-N-{3-[3-fluoro-4-(4-oxo-piperidin-1-yl)-phenyl]-2-oxo-oxazolidin-5-ylmethyl}-acetamide (Compound No. 7) which was synthesized in Example 3, and the mixture was stirred at room temperature for 14 h under 2 atm hydrogen atmosphere. Sodium hydrogencarbonate was added and the mixture was stirred for 10 min. Thereafter, the catalyst was filtered off and the solvent was evaporated under vacuum. The residue was purified by alumina column chromatography (solvent: chloroform/methanol=100/1–30/1) to afford the title compound (900 mg) in a yield of 43%.

EXAMPLE 19

Preparation of (S)-N-{3-[4-(4-dimethylamino-piperidin-1-yl)-3-fluoro-phenyl]-2-oxo-oxazolidin-5-ylmethyl}-acetamide (Compound No. 71)

Formaldehyde (37% aq. sol., 0.4 ml) and sodium cyanoboron hydride (138 mg) were successively added to an acetonitrile suspension (3 ml) of 400 mg of the (S)-N-{3-[3-fluoro-4-(4-methylamino-piperidin-1-yl)-phenyl]-2-oxo-oxazolidin-5-ylmethyl}-acetamide (Compound No. 70) which was synthesized in Example 18, and the mixture was stirred at room temperature for 48 h. Methanol was added and the mixture was stirred for 10 min. Thereafter, alumina (5 g) was added and the residue was evaporated under vacuum. The residue was purified by alumina column chromatography (solvent: chloroform/methanol=100/1) to afford the title compound (363 mg) in a yield of 87%.

EXAMPLE 20

Preparation of (S)-N-(3-{3-fluoro-4-[4-(thiazol-2-ylamino)-piperidin-1-yl]-phenyl}-2-oxo-oxazolidin-5-ylmethyl)-acetamide (Compound No. 67)

Potassium carbonate (296 mg) and 2-bromothiasole (258 mg) were added to a dimethylformamide solution (5 ml) of 500 mg of the (S)-N-{3-[4-(4-amino-piperidin-1-yl)-3-fluoro-phenyl]-2-oxo-oxazolidin-5-ylmethyl}-acetamide (Compound No. 6) which was synthesized in Example 4, and the mixture was stirred at 100° C. for 2 days. The reaction mixture was cooled to room temperature and filtered. The filtrate was concentrated under vacuum and the residue was purified by silica gel column chromatography (dichloromethane/methanol=97/3–4/1) to afford the title compound (73 mg) in a yield of 12%.

EXAMPLE 21

Preparation of (S)-N-{3-[4-(4-cyanoimino-piperidin-1-yl)-3-fluoro-phenyl]-2-oxo-oxazolidin-5-ylmethyl}-acetamide (Compound No. 59)

Cyanamide (601 mg) and 500 mg of the (S)-N-{3-[3-fluoro-4-(4-oxo-piperidin-1-yl)-phenyl]-2-oxo-oxazolidin-5-ylmethyl}-acetamide (Compound No. 7) which was synthesized in Example 3 were added to benzene (70 ml), and the mixture was heated under reflux for 2 h, with water being removed continuously by means of a water separator. The reaction mixture was cooled to room temperature and the resulting crystal was collected by filtration. After being washed with water, the crystal was dried overnight at 40° C. under vacuum to afford the title compound (423 mg) in a yield of 79%.

EXAMPLE 22

Preparation of (S)-N-{3-[4-(4-dimethylaminomethyleneamino-piperidin-1-yl)-3-fluoro-phenyl]-2-oxo-oxazolidin-5-ylmethyl}-acetamide (Compound No. 72)

N,N-dimethylformamide dimethylacetal (0.8 ml) and 1.0 g of the (S)-N-{3-[4-(4-amino-piperidin-1-yl)-3-fluorophenyl]-2-oxo-oxazolidin-5-ylmethyl}-acetamide (Compound No. 6) which was synthesized in Example 4 were added to toluene (10 ml) and the mixture was heated under reflux for 24 h. The reaction mixture was cooled to room temperature and concentrated under vacuum. The residue was washed with hexane to remove excess dimethylacetal. The resulting precipitate was suspended in dichloromethane and the insolubles were separated by filtration. The filtrate was concentrated under vacuum to afford the title compound (985 mg) in a yield of 84%.

EXAMPLE 23

Preparation of (S)-2-fluoro-N-{3-[3-fluoro-4-(4-oxo-piperidin-1-yl)-phenyl]-2-oxo-oxazolidin-5-ylmethyl}-acetamide (Compound No. 73)

Starting with the 3-[4-(1,4-dioxa-8-aza-spiro[4.5]dec-8-yl)-3-fluoro-phenyl]-5-hydroxymethyl-oxazolidin-2-one which was formed as an intermediate in Example 3, the procedure of Example 1 was repeated to produce an azide compound in a yield of 90%. The azide compound (1.5 g) was reduced with triphenylphosphine/tetrahydrofuran/water by the same method as in Example 10 to provide a primary amine compound. The amine compound and triethylamine (1.2 ml) were added to dry dichloromethane (20 ml) and benzyloxyacetyl chloride (1.20 g) was subsequently added at 0° C. The reaction mixture was stirred overnight at room temperature and the resulting precipitate was filtered off. The filtrate was concentrated under vacuum and the residue was purified by silica gel column chromatography (methanol/dichloromethane=5/95) to afford a benzyloxyacetamide compound (2.7 g) in a yield of 100%. The benzyloxyacetamide compound (1.9 g) was dissolved in a mixed solvent consisting of methanol (30 ml) and dichloromethane (5 ml). To the solution, 10% palladium hydroxide/carbon (340 mg) was added and the mixture was stirred for 2 days under 3 atm hydrogen atmosphere. The palladium hydroxide was filtered off and the filtrate was concentrated under vacuum. The residue was purified by silica gel column chromatography (methanol/dichloromethane=7/93) to afford an α-hydroxyacetamide compound (780 mg) in a yield of 49%. To a tetrahydrofuran solution (10 ml) of the α-hydroxyacetamide compound (530 mg), p-toluenesulfonyl fluoride (450 mg) and tetrabutylammonium fluoride (1.0M tetrahydrofuran solution; 3.3 ml) were added and the mixture was heated under reflux overnight. The reaction mixture was cooled to room temperature and concentrated under vacuum. The residue was purified by silica gel column chromatography (hexane/acetone=2/3) to afford a monofluoroacetamide compound (562 mg) in a yield of 100%. To 10 ml of an acetone solution of the monofluoroacetamide compound, p-toluenesulfonic acid monohydrate (580 mg) and water (3 ml) were added and the mixture was heated under reflux for 2.5 h. The reaction mixture was cooled to room temperature, neutralized with solid sodium hydrogencarbonate, and concentrated under vacuum. Water was removed by azeotropy with toluene and the residue was purified by silica gel column chromatography (hexane/acetone=1/1) to afford the title compound (408 mg) in a yield of 81%.

The compounds prepared in Examples 1–23, as well as several compounds that were synthesized by similar methods were found to have the following nuclear magnetic resonance spectrum ($^1$H-NMR) data.

Compound No. 1:

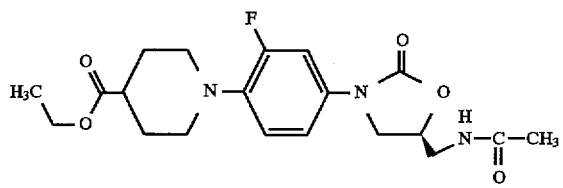

$^1$H NMR (CDCl$_3$) δ ppm: 1.27 (3H, t, J=7.2 Hz), 1.86–2.07 (4H, m), 2.02 (3H, s), 2.37–2.48 (1H, m), 2.68–2.77 (2H, m), 3.34–3.41 (2H, m), 3.55–3.76 (3H, m), 4.01 (1H, dd, J=8.9, 8.9 Hz), 4.16 (2H, q, J=7.2 Hz), 4.71–4.81 (1H, m), 6.12 (1H, br s), 6.92 (1H, dd, J=8.9, 8.9 Hz), 7.06 (1H, ddd, J=2.4, 2.4, 8.9 Hz), 7.40 (1H, dd, J=2.4, 13.8 Hz).

Compound No. 2

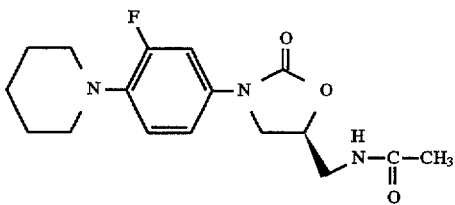

$^1$H NMR (CDCl$_3$) δ ppm: 1.52–1.62 (2H, m), 1.65–1.78 (4H, m), 2.02 (3H, s), 2.96–3.00 (4H, m), 3.55–3.77 (3H, m), 4.01 (1H, dd, J=8.9, 8.9 Hz), 4.71–4.80 (1H, m), 6.28 (1H, br s), 6.93 (1H, dd, J=8.9, 8.9 Hz), 7.05 (1H, ddd, J=2.4, 2.4, 8.9 Hz), 7.38 (1H, dd, J=2.4, 14.3 Hz).

Compound No. 3

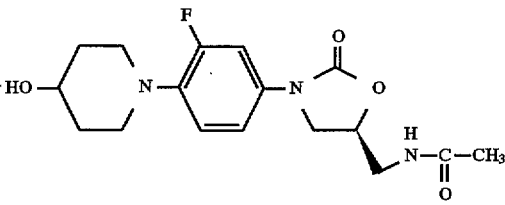

$^1$H NMR (CDCl$_3$) δ ppm: 1.69–1.82 (2H, m), 1.99–2.07 (2H, m), 2.02 (3H, s), 2.78–2.87 (2H, m), 3.28–3.35 (2H, m), 3.54–3.76 (3H, m), 3.81–3.90 (1H, m), 4.02 (1H, dd, J=8.9, 8.9 Hz), 4.71–4.81 (1H, m), 6.08 (1H, t, J=5.9 Hz), 6.94 (1H, dd, J=8.9, 8.9 Hz), 7.06 (1H, ddd, J=2.2, 2.2, 8.9 Hz), 7.41 (1H, dd, J=2.2, 14.3 Hz).

Compound No. 4

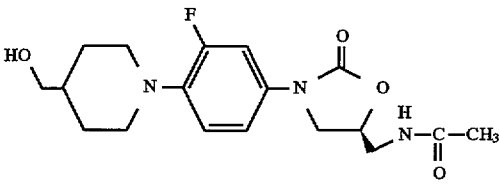

$^1$H NMR (DMSO-d$_6$) δ ppm: 1.22–1.36 (2H, m), 1.41–1.53 (1H, m), 1.73–1.77 (2H, m), 1.83 (3H, s), 2.55–2.63 (2H, m), 3.25–3.34 (4H, m), 3.39 (2H, dd, J=5.4, 5.4 Hz), 3.69 (1H, dd, J=6.5, 8.9 Hz), 4.07 (1H, dd, J=8.9, 8.9 Hz), 4.48 (1H, t, J=5.4 Hz), 4.65–4.74 (1H, m), 7.05 (1H, dd, J=9.2, 9.2 Hz), 7.15 (1H, dd, J=2.7, 9.2 Hz), 7.45 (1H, dd, J=2.2, 14.9 Hz), 8.23 (1H, t, J=5.9 Hz).

Compound No. 5

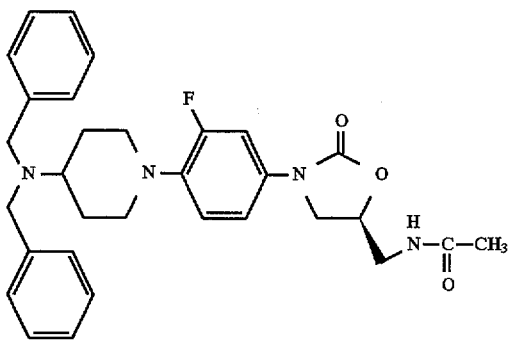

$^1$H NMR (CDCl$_3$) δ ppm: 1.84–1.92 (4H, m), 2.00 (3H, s), 2.49–2.68 (3H, m), 3.40–3.46 (2H, m), 3.53–3.74 (3H, m), 3.69 (s and s, 2H and 2H), 3.98 (1H, dd, J=9.2, 9.2 Hz), 4.69–4.78 (1H, m), 6.26 (1H, t, J=5.9 Hz), 6.87 (1H, dd, J=9.2, 9.2 Hz), 7.01 (1H, dd, J=2.2, 9.2 Hz), 7.16–7.40 (11H, m).

Compound No. 6

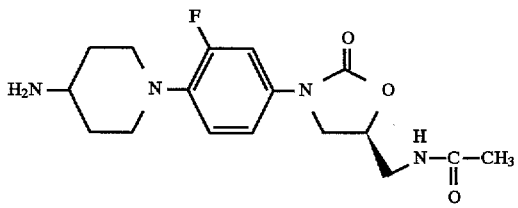

$^1$H NMR (DMSO-d$_6$) δ ppm: 1.55–1.69 (2H, m), 1.84 (3H, s), 1.92–1.99 (2H, m), 2.65–2.74 (2H, m), 2.98–3.07 (1H, m), 3.28–3.33 (2H, m), 3.38–3.74 (3H, m), 4.08 (1H, dd, J=9.2, 9.2 Hz), 4.66–4.75 (1H, m), 7.07 (1H, dd, J=9.2, 9.2 Hz), 7.17 (1H, dd, J=2.4, 9.2 Hz), 7.47 (1H, dd, J=2.4, 14.9 Hz), 8.28 (1H, t, J=5.7 Hz).

Compound No. 7

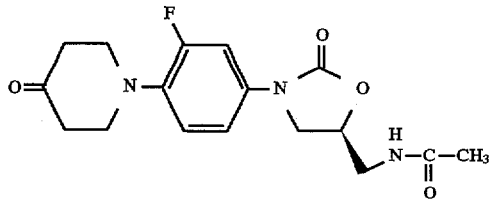

$^1$H NMR (CDCl$_3$) δ ppm: 2.03 (3H, s), 2.60–2.65 (4H, m), 3.35–3.40 (4H, m), 3.57–3.79 (3H, m), 4.03 (1H, dd, J=8.9, 8.9 Hz), 4.73–4.82 (1H, m), 6.14 (1H, t, J=5.9 Hz), 6.97 (1H, dd, J=9.2, 9.2 Hz), 7.09 (1H, ddd, J=2.2, 2.2, 9.2 Hz), 7.41 (1H, dd, J=2.2, 14.0 Hz).

Compound No. 8

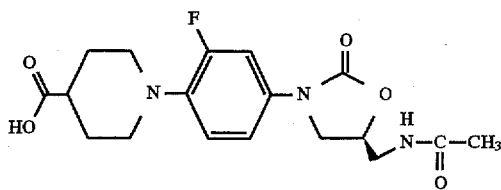

$^1$H NMR (DMSO-d$_6$) δ ppm: 1.60–1.74 (2H, m), 1.83–1.97 (3H, m), 1.84 (3H, s), 2.57–2.65 (2H, m), 3.19–3.25 (2H, m) 3.36–3.41 (2H, m), 3.73 (1H, dd, J=6.5, 8.9 Hz), 4.07 (1H, dd, J=8.9, 8.9 Hz), 4.65–4.74 (1H, m), 7.03 (1H, dd, J=9.2, 9.2 Hz), 7.14 (1H, dd, J=2.4, 9.2 Hz), 7.44 (1H, dd, J=2.4, 14.9 Hz), 8.39 (1H, t, J=5.7 Hz).

Compound No. 9

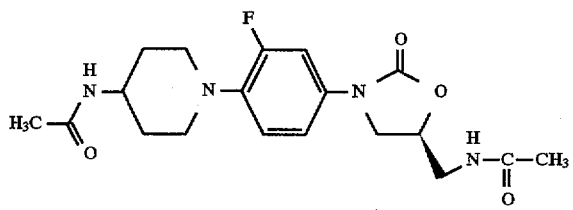

$^1$H NMR (DMSO-d$_6$) δ ppm: 1.45–1.60 (2H, m), 1.76–1.90 (2H, m), 1.81 (3H, s), 1.83 (3H, s), 2.67–2.75 (2H, m), 3.22–3.29 (2H, m), 3.38–3.42 (2H, m), 3.61–3.73 (2H, m), 4.08 (1H, dd, J=9.2, 9.2 Hz), 4.66–4.75 (1H, m), 7.07 (1H, dd, J=9.2, 9.2 Hz), 7.16 (1H, dd, J=2.4, 9.2 Hz), 7.47 (1H, dd, J=2.4, 14.9 Hz), 7.85 (1H, d, J=8.1 Hz), 8.24 (1H, t, J=5.7 Hz).

Compound No. 10

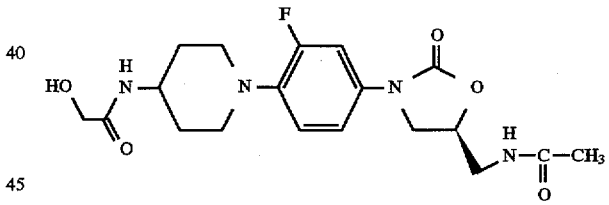

$^1$H NMR (DMSO-d$_6$) δ ppm: 1.71–1.87 (4H, m), 1.92 (3H, s), 2.76–2.84 (2H, m), 3.32–3.39 (2H, m), 3.47–3.51 (2H, m), 3.76–3.86 (2H, m), 3.90 (2H, d, J=5.9 Hz), 4.16 (1H, dd, J=8.9, 8.9 Hz), 4.74–4.83 (1H, m), 5.52 (1H, t, J=5.9 Hz), 7.15 (1H, dd, J=9.2, 9.2 Hz), 7.24 (1H, dd, J=1.8, 9.2 Hz), 7.55 (1H, dd, J=1.8, 14.9 Hz), 7.74 (1H, d, J=7.8 Hz), 8.32 (1H, t, J=5.7 Hz).

Compound No. 11

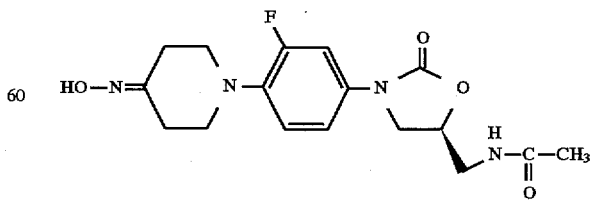

$^1$H NMR (DMSO-d$_6$) δ ppm: 1.83 (3H, s), 2.25–2.38 (2H, m), 2.61–2.65 (2H, m), 3.00–3.11 (4H, m), 3.38–3.42 (2H, m), 3.70 (1H, dd, J=6.5, 9.2 Hz), 4.08 (1H, dd, J=9.2, 9.2 Hz), 4.64–4.75 (1H, m), 7.09 (1H, dd, J=8.9, 8.9 Hz), 7.17 (1H, dd, J=2.2, 8.9 Hz), 7.49 (1H, dd, J=2.2, 14.9 Hz) 8.24 (1H, t, J=4.9 Hz), 10.42 (1H, s), Compound No. 29

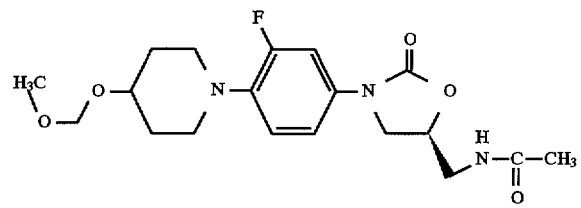

$^1$H NMR (CDCl$_3$) δ ppm: 1.71–1.88 (2H, m), 2.00–2.10 (2H, m), 2.02 (3H, s), 2.79–2.88 (2H, m), 3.26–3.37 (2H, m), 3.40 (3H, s), 3.55–3.77 (4H, m), 4.01 (1H, dd, J=8.9, 8.9 Hz), 4.70–4.81 (1H, m), 4.73 (2H, s), 6.22 (1H, br s), 6.94 (1H, dd, J=9.2, 9.2 Hz), 7.05 (1H, ddd, J=1.5, 1.5, 8.9 Hz), 7.40 (1H, dd, J=2.4, 14.3 Hz).

Compound No. 30

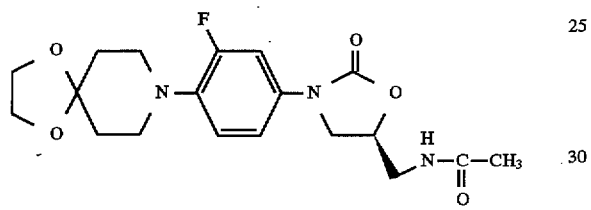

$^1$H NMR (CDCl$_3$) δ ppm: 1.87–1.91 (4H, m), 2.02 (3H, s), 3.11–3.15 (2H, m), 3.56–3.78 (3H, m), 4.00 (4H, s), 4.01 (1H, t, J=8.9 Hz), 4.72–4.81 (1H, m), 6.49 (1H, t, J=6.2 Hz), 6.94 (1H, dd, J=8.9, 8.9 Hz), 7.04 (1H, dd, J=3.0, 8.9 Hz), 7.39 (1H, dd, J=2.6, 14.2 Hz).

Compound No. 31

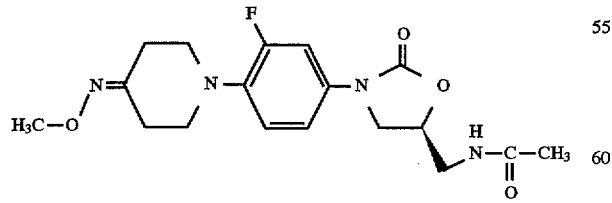

$^1$H NMR (CDCl$_3$) δ ppm: 2.02 (3H, s), 2.48–2.52 (2H, m), 2.72–2.77 (2H, m), 3.09–3.13 (2H, m), 3.16–3.20 (2H, m), 3.56–3.69 (2H, m), 3.75 (1H, dd, J=6.6, 9.2 Hz), 3.86 (3H, s), 4.02 (1H, dd, J=9.2, 9.2 Hz), 4.72–4.82 (1H, m), 6.25 (1H, br s), 6.92 (1H, dd, J=8.9, 8.9 Hz), 7.06 (1H, dd, J=2.6, 8.8 Hz), 7.43 (1H, dd, J=2.4, 14.3 Hz).

Compound No. 32

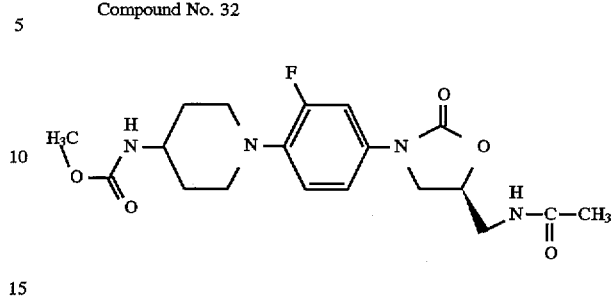

$^1$H NMR (DMSO-d$_6$) δ ppm: 1.49–1.61 (2H, m), 1.80–1.90 (2H, m), 1.83 (3H, s), 2.66–2.73 (2H, m), 3.23–3.31 (2H, m), 3.38–3.42 (2H, m), 3.53 (3H, s), 3.69 (1H, dd, J=6.5, 8.9 Hz), 4.07 (1H, dd, J=9.0, 9.0 Hz), 4.65–4.73 (1H, m), 7.07 (1H, dd, J=9.5, 9.5 Hz), 7.15 (1H, dd, J=2.2, 9.2 Hz), 7.46 (1H, dd, J=2.4, 14.9 Hz), 8.23 (1H, t, J=5.7 Hz).

Compound No. 33

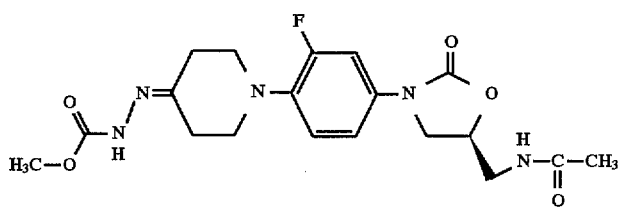

$^1$H NMR (DMSO-d$_6$) δ ppm: 1.83 (3H, s), 2.42–2.46 (2H, m), 2.56–2.60 (2H, m), 3.03–3.07 (2H, m), 3.10–3.15 (2H, m), 3.38–3.42 (2H, m), 3.70 (1H, dd, J=6.3, 8.8 Hz), 4.08 (1H, dd, J=8.9, 8.9 Hz), 4.66–4.75 (1H, m), 7.09 (1H, dd, J=9.0, 9.0 Hz), 7.17 (1H, dd, J=2.4, 8.9 Hz), 7.49 (1H, dd, J=2.4, 14.6 Hz) 8.23 (1H, t, J=5.8 Hz).

Compound No. 34

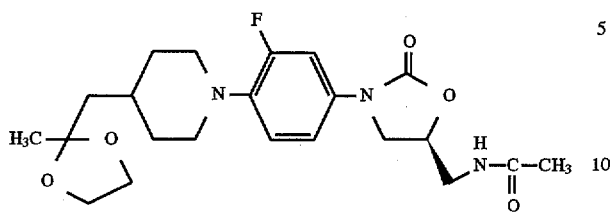

¹H NMR (CDCl₃) δ ppm: 1.35 (3H, s), 1.40–1.75 (5H, m), 1.90 (2H, d, J=12.2 Hz), 2.02 (3H, s), 2.60–2.68 (2H, m), 3.33–3.38 (2H, m), 3.55–3.77 (3H, m), 3.90–3.96 (4H, m), 4.01 (1H, dd, J=8.8, 8.8 Hz), 4.71–4.80 (1H, m), 6.34 (1H, br s), 6.92 (1H, dd, J=8.9, 8.9 Hz), 7.05 (1H, br d, J=8.9 Hz), 7.38 (1H, dd, J=2.4, 14.6 Hz).

Compound No. 35

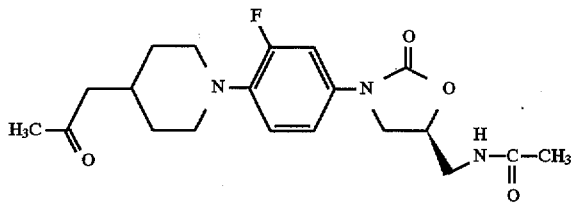

¹H NMR (CDCl₃) δ ppm: 1.36–1.51 (2H, m), 1.77–1.82 (2H, m), 1.91–2.05 (1H, m), 2.02 (3H, s), 2.16 (3H, s), 2.43 (2H, d, J=6.8 Hz), 2.63–2.72 (2H, m), 3.34–3.38 (2H, m), 3.55–3.77 (3H, m), 4.01 (1H, dd, J=9.0, 9.0 Hz), 4.72–4.81 (1H, m), 6.28 (1H, br s), 6.92 (1H, dd, J=9.0, 9.0 Hz), 7.05 (1H, ddd, J=1.5, 1.5, 8.9 Hz), 7.39 (1H, dd, J=2.3, 14.2 Hz).

Compound No. 36

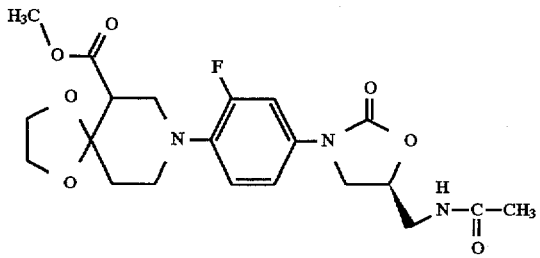

¹H NMR (CDCl₃) δ ppm: 1.66–1.92 (1H, m), 1.93 (3H, s), 2.02–2.09 (1H, m), 2.97–3.12 (2H, m), 3.23 (1H, m), 3.39 (2H, d, J=6.8 Hz), 3.57–3.77 (3H, m), 3.74 (3H, s), 4.02 (5H, m), 4.77 (1H, m), 6.20 (1H, t, J=5.9 Hz), 6.95 (1H, t, J=8.6 Hz), 7.05 (1H, dd, J=2.4, 8.6 Hz), 7.41 (1H, dd, J=2.4, 13.8 Hz).

Compound No. 37

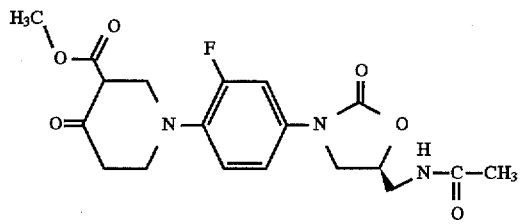

¹H NMR (CDCl₃) δ ppm: 2.02 (3H, s), 2.49–2.74 (2H, m), 3.27–3.39 (2H, m), 3.57–3.71 (4H, m), 3.73 (2H, d, J=6.8 Hz), 3.78 (3H, s), 4.02 (1H, t, J=8.9 Hz), 4.78 (1H, m), 6.45 (1H, broad), 6.97 (1H, t, J=8.6 Hz), 7.06 (1H, dd, J=2.4, 8.6 Hz), 7.43 (1H, dd, J=2.4, 13.8 Hz).

Compound No. 38

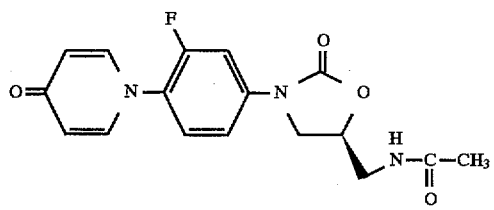

¹H NMR (CDCl₃) δ ppm: 2.04 (3H, s), 3.68 (2H, t, J=5.7 Hz), 3.89 (1H, dd, J=6.8, 9.5 Hz), 4.11 (1H, t, J=9.5 Hz), 4.85 (1H, m), 6.50 (2H, d, J=7.8 Hz), 7.15 (1H, t, J=5.9 Hz), 7.34 (1H, dd, J=2.4, 8.6 Hz), 7.38 (1H, t, J=8.6 Hz), 7.47 (2H, d, J=7.8 Hz), 7.74 (1H, dd, J=2.4, 13.8 Hz).

Compound No. 39

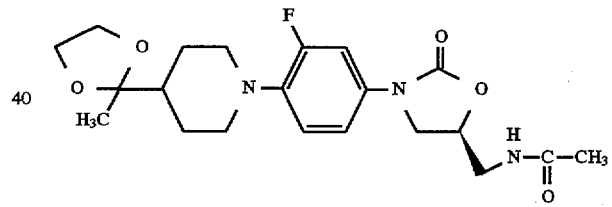

¹H NMR (CDCl₃) δ ppm: 1.30 (3H, s), 1.60–1.88 (5H, m), 2.02 (3H, s), 2.55–2.64 (2H, m), 3.44–3.48 (2H, m), 3.55–3.77 (3H, m), 3.89–4.04 (5H, m), 4.72–4.81 (1H, m), 6.39 (1H, br s), 6.92 (1H, dd, J=9.0, 9.0 Hz), 7.05 (1H, dd, J=2.2, 9.2 Hz), 7.38 (1H, dd, J=2.8, 14.2 Hz).

Compound No. 40

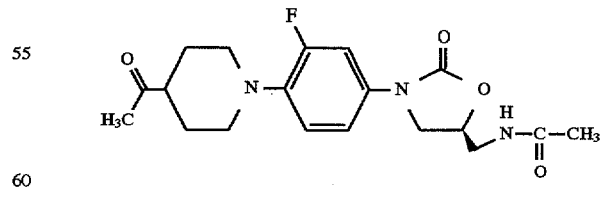

¹H NMR (CDCl₃) δ ppm: 1.76–2.00 (4H, m), 2.02 (3H, s), 2.19 (3H, s), 2.38–2.49 (1H, m), 2.66–2.76 (2H, m), 3.40–3.44 (2H, m), 3.56–3.77 (3H, m), 4.01 (1H, dd, J=8.8, 8.8 Hz), 4.72–4.81 (1H, m), 6.35 (1H, br s), 6.92 (1H, dd, J=8.9, 8.9 Hz), 7.05 (1H, br d, J=8.9 Hz), 7.39 (1H, dd, J=2.2, 14.6 Hz).

Compound No. 41

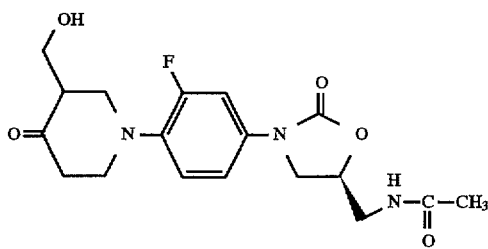

¹H NMR (CDCl₃) δ ppm: 2.02 (3H, s), 2.54 (1H, m), 2.64–2.92 (2H, m), 3.05–3.20 (2H, m), 3.57–4.06 (7H, m), 4.03 (1H, t, J=9.2 Hz), 4.78 (1H, m), 6.27 (1H, br s), 6.98 (1H, t, J=8.6 Hz), 7.08 (1H, dd, J=2.4, 8.6 Hz), 7.47 (1H, dd, J=2.4, 13.8 Hz).

Compound No. 42

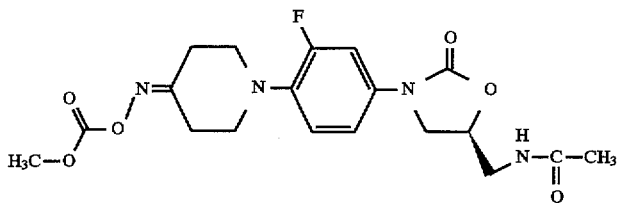

¹H NMR (CDCl₃) δ ppm: 2.02 (3H, s), 2.66–2.70 (2H, m), 2.84–2.88 (2H, m), 3.15–3.19 (2H, m), 3.23–3.27 (2H, m), 3.56–3.78 (3H, m), 3.90 (3H, s), 4.02 (1H, dd, J=9.0, 9.0 Hz), 4.73–4.82 (1H, m), 6.15 (1H, br s), 6.93 (1H, dd, J=9.0, 9.0 Hz), 7.07 (1H, ddd, J=1.1, 1.1, 8.9 Hz), 7.46 (1H, dd, J=2.6, 14.2 Hz).

Compound No. 43

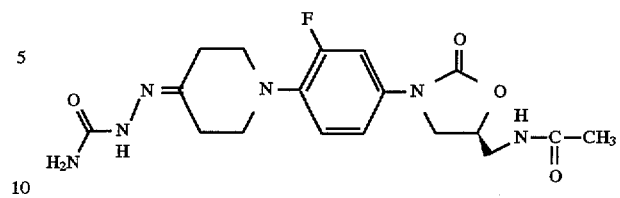

¹H NMR (DMSO-d₆) δ ppm: 1.83 (3H, s), 2.42–2.46 (2H, m), 2.55–2.60 (2H, m), 3.03–3.07 (2H, m), 3.10–3.14 (2H, m), 3.38–3.42 (2H, m), 3.70 (1H, dd, J=6.2, 9.2 Hz), 3.90 (3H, s), 4.08 (1H, dd, J=9.0, 9.0 Hz), 4.66–4.73 (1H, m), 6.23 (2H, s), 7.09 (1H, dd, J=8.9, 8.9 Hz), 7.17 (1H, dd, J=2.4, 8.9 Hz), 7.49 (1H, dd, J=2.4, 14.6 Hz) 8.23 (1H, t, J=5.7 Hz), 9.25 (1H, s).

Compound No. 44

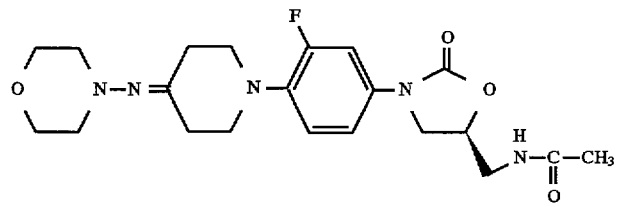

¹H NMR (DMSO-d₆) δ ppm: 1.83 (3H, s), 2.41 (2H, t, J=5.9 Hz), 2.62 (4H, m), 2.73 (2H, t, J=5.9 Hz), 3.06 (2H, t, J=5.9 Hz), 3.12 (2H, t, J=5.9 Hz), 3.40 (2H, t, J=5.4 Hz), 3.66 (5H, m), 4.08 (1H, t, J=8.9 Hz), 4.70 (1H, m), 7.09 (1H, t, J=9.2 Hz), 7.17 (1H, dd, J=2.4, 9.2 Hz), 7.49 (1H, dd, J=2.2, 14.9 Hz), 8.23 (1H, t, J=5.7 Hz).

Compound No. 45

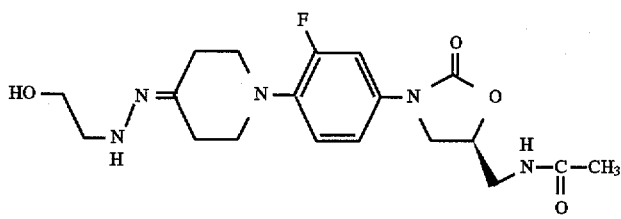

¹H NMR (DMSO-d₆) δ ppm: 1.83 (3H, s), 2.35 (2H, t, J=5.7 Hz), 2.48 (2H, t, J=5.7 Hz), 3.06 (6H, m), 3.40 (2H, t, J=5.9 Hz), 3.50 (2H, dd, J=5.9, 11.9 Hz), 3.70 (1H, dd, J=6.5, 8.9 Hz), 4.08 (1H, t, J=8.9 Hz), 4.67 (1H, t, J=5.4 Hz), 4.71 (1H, m), 5.77 (1H, t, J=4.9 Hz), 7.07 (1H, t, J=9.2 Hz), 7.16 (1H, dd, J=2.4, 9.2 Hz), 7.48 (1H, dd, J=2.2, 14.9 Hz), 8.23 (1H, t, J=5.7 Hz).

Compound No. 46

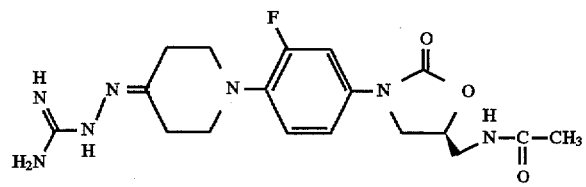

¹H NMR (DMSO-d₆) δ ppm: 1.83 (3H, s), 2.42–2.47 (2H, m), 2.73–2.77 (2H, m), 3.01–3.05 (2H, m), 3.09–3.12 (2H, m), 3.38–3.42 (2H, m), 3.71 (1H, dd, J=6.2, 9.5 Hz), 4.08 (1H, dd, J=9.0, 9.0 Hz), 4.66–4.75 (1H, m), 5.88 (3H, br s), 7.09 (1H, dd, J=9.3, 9.3 Hz), 7.16 (1H, dd, J=2.4, 8.6 Hz), 7.49 (1H, dd, J=2.3, 14.7 Hz) 8.25 (1H, t, J=5.7 Hz).

Compound No. 47

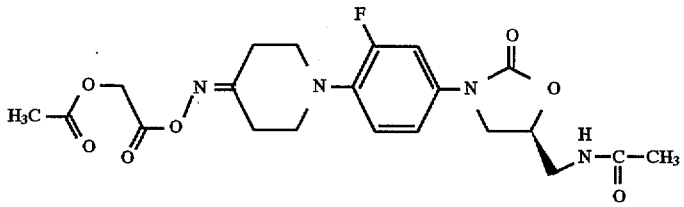

¹H NMR (CDCl₃) δ ppm: 2.02 (3H, s), 2.19 (3H, s), 2.65–2.69 (2H, m), 2.81–2.86 (2H, m), 3.16–3.20 (2H, m), 3.23–3.27 (2H, m), 3.57–3.79 (3H, m), 4.02 (1H, dd, J=9.0, 9.0 Hz), 4.73–4.82 (1H, m), 4.79 (2H, s), 6.25 (1H, t, J=6.3 Hz), 6.93 (1H, dd, J=8.9, 8.9 Hz), 7.08 (1H, ddd, J=1.2, 1.2, 8.8 Hz), 7.46 (1H, dd, J=2.4, 14.0 Hz).

Compound No. 48

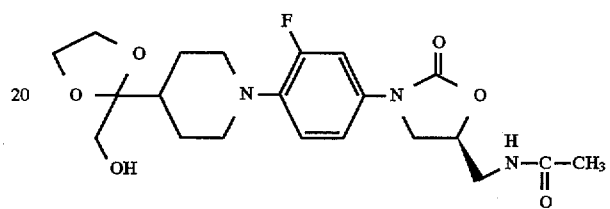

¹H NMR (DMSO-d₆) δ ppm: 1.42–1.54 (2H, m), 1.72–1.89 (3H, m), 1.83 (3H, s), 2.51–2.59 (2H, m), 3.32–3.42 (4H, m), 3.69 (1H, dd, J: 6.6, 9.0 Hz), 3.82–3.96 (4H, m), 4.07 (1H, dd, J=9.0, 9.0 Hz), 4.65–4.75 (1H, m), 4.75 (1H, t, J=6.1 Hz), 7.04 (1H, dd, J=9.3, 9.3 Hz), 7.14 (1H, dd, J=2.4, 8.6 Hz), 7.45 (1H, dd, J=2.4, 15.1 Hz), 8.23 (1H, t, J=5.8 Hz).

Compound No. 49

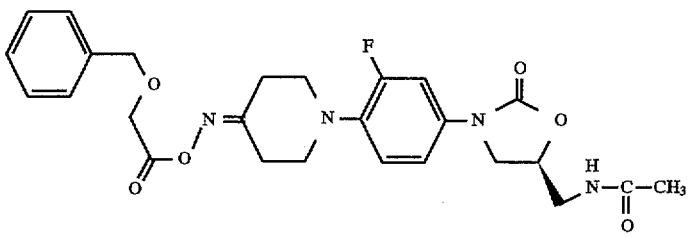

¹H NMR (CDCl₃) δ ppm: 2.02 (3H, s), 2.65–2.70 (2H, m), 2.80–2.84 (2H, m), 3.13–3.18 (2H, m), 3.22–3.26 (2H, m), 3.56–3.79 (3H, m), 4.01 (1H, dd, J=9.0, 9.0 Hz), 4.27 (2H, s), 4.69 (2H, s), 4.72–4.82 (1H, m), 6.33 (1H, t, J=6.3 Hz), 6.92 (1H, dd, J=9.0, 9.0 Hz), 7.07 (1H, dd, J=2.0, 8.8 Hz), 7.29–7.48 (6H, m).

Compound No. 50

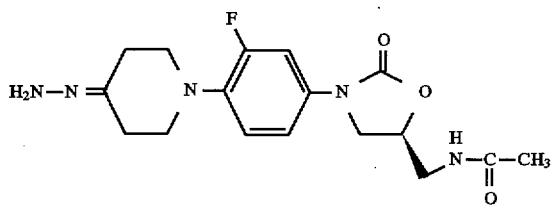

Compound No. 51

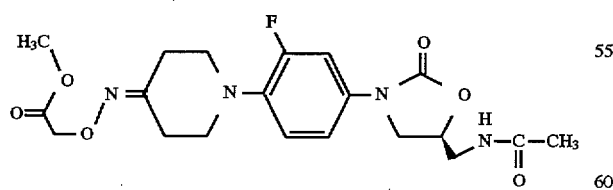

¹H NMR (CDCl₃) δ ppm: 2.02 (3H, s), 2.48–2.52 (2H, m), 2.81–2.86 (2H, m), 3.13–3.23 (4H, m), 3.56–3.78 (3H, m), 3.77 (3H, s), 4.05 (1H, dd, J=8.4, 8.4 Hz), 4.61 (2H, s), 4.78–4.82 (1H, m), 6.32 (1H, t, J=5.8 Hz), 6.93 (1H, dd, J=9.0, 9.0 Hz), 7.06 (1H, dd, J=1.5, 8.8 Hz), 7.43 (dd, 1H, J=2.6, 14.2 Hz).

Compound No. 52

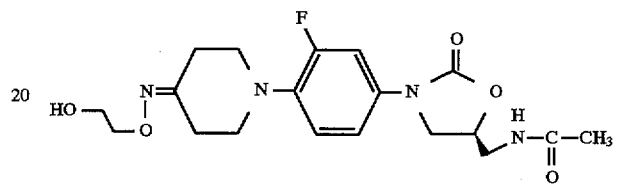

¹H NMR (CDCl₃) δ ppm: 2.02 (3H, s), 2.48–2.53 (2H, m), 2.76–2.80 (2H, m), 3.11–3.21 (4H, m), 3.56–3.78 (3H, m), 3.87–3.92 (2H, m), 4.02 (1H, dd, J=9.0, 9.0 Hz), 4.16–4.19 (2H, m), 4.72–4.82 (1H, m), 6.12 (1H, t, J=6.1 Hz), 6.93 (1H, dd, J=9.0, 9.0 Hz), 7.09 (1H, dd, J=1.4, 8.6 Hz), 7.44 (dd, 1H, J=2.6, 13.9 Hz).

Compound No. 53

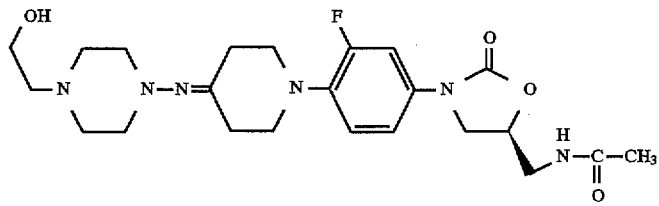

¹H NMR (DMSO-d₆) δ ppm: 1.83 (3H, s), 2.54 (2H, t, J=5.4 Hz), 2.69 (2H, t, J=5.4 Hz), 3.06 (2H, t, J=5.4 Hz), 3.18 (2H, t, J=5.4 Hz), 3.40 (2H, t, J=5.4 Hz), 3.71 (1H, dd, J=6.2, 8.6 Hz), 4.08 (1H, t, J=8.6 Hz), 4.70 (1H, m), 7.11 (1H, t, J=9.2 Hz), 7.17 (1H, dd, J=2.4, 9.2 Hz), 7.49 (1H, dd, J=2.2, 14.9 Hz), 8.23 (1H, t, J=5.9 Hz).

¹H NMR (CDCl₃) δ ppm: 2.02 (3H, s), 2.54–2.84 (14H, m), 3.14 (2H, t, J=5.7 Hz), 3.22 (2H, t, J=5.7 Hz), 3.61 (4H, m), 3.75 (1H, dd, J=6.2, 8.6 Hz), 4.02 (1H, t, J=8.6 Hz), 4.78 (1H, m), 6.13 (1H, br s), 6.93 (1H, t, J=8.6 Hz), 7.07 (1H, dd, J=2.4, 8.6 Hz), 7.44 (1H, dd, J=2.4, 13.8 Hz).

Compound No. 54

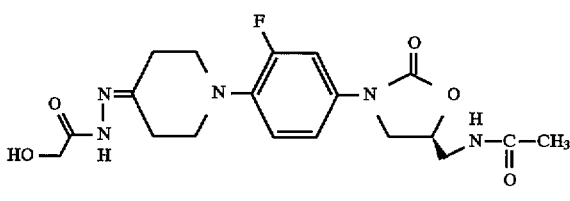

¹H NMR (DMSO-d₆) δ ppm: 1.83 (3H, s), 2.55 (4H, m), 3.03 (2H, m), 3.19 (2H, m), 3.40 (2H, m), 3.70 (1H, m), 4.08 (1H, t, J=9.2 Hz), 4.12 (2H, s), 4.71 (1H, m), 7.13 (2H, m), 7.48 (1H, dd, J=2.2, 14.9 Hz), 8.23 (1H, t, J=5.7 Hz).

Compound No. 55

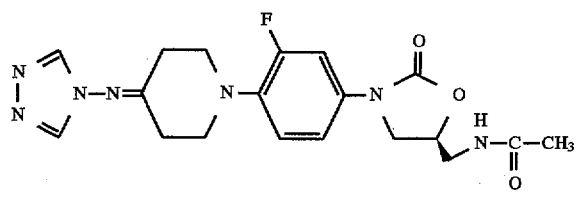

¹H NMR (CDCl₃+CD₃OD) δ ppm: 2.02 (3H, s), 2.63–2.68 (2H, m), 2.85–2.89 (2H, m), 3.18–3.22 (2H, m), 3.35–3.40 (2H, m), 3.54–3.80 (3H, m), 4.04 (1H, dd, J=9.0, 9.0 Hz), 4.73–4.82 (1H, m), 6.96 (1H, dd, J=9.0, 9.0 Hz), 7.10 (1H, ddd, J=1.2, 1.2, 8.6 Hz), 7.30 (1H, br s), 7.47 (1H, dd, J=2.4, 14.0 Hz), 8.22 (2H, s).

Compound No. 56

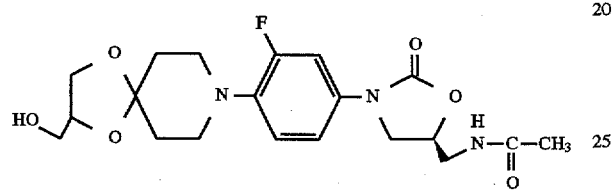

¹H NMR (DMSO-d₆) δ ppm: 1.64–1.70 (4H, m), 1.83 (3H, s), 2.98–3.07 (4H, m), 3.38–3.51 (4H, m), 3.67–3.74 (2H, m), 3.99–4.14 (3H, m), 4.67–4.72 (1H, m), 4.84 (1H, t, J=5.5 Hz), 7.05–7.18 (2H, m), 7.46 (1H, dd, J=2.4, 14.6 Hz), 8.23 (1H, t, J=5.8 Hz).

Compound No. 57

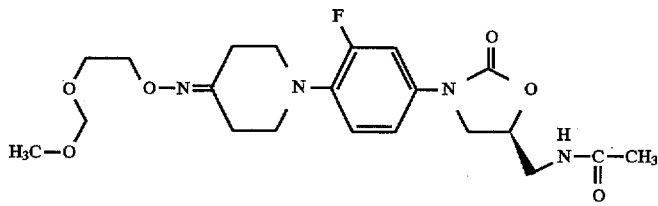

¹H NMR (CDCl₃) δ ppm: 2.02 (3H, s), 2.48–2.53 (2H, m), 2.77–2.81 (2H, m), 3.09–3.20 (4H, m), 3.38 (3H, s), 3.56–3.81 (5H, m), 4.02 (1H, dd, J=9.0, 9.0 Hz), 4.21–4.25 (1H, m), 4.68 (2H, s), 4.72–4.82 (1H, m), 6.22 (1H, t, J=6.2 Hz), 6.92 (1H, dd, J=9.0, 9.0 Hz), 7.07 (1H, dd, J=2.2, 9.5 Hz), 7.43 (1H, dd, J=2.4, 14.0 Hz).

Compound No. 58

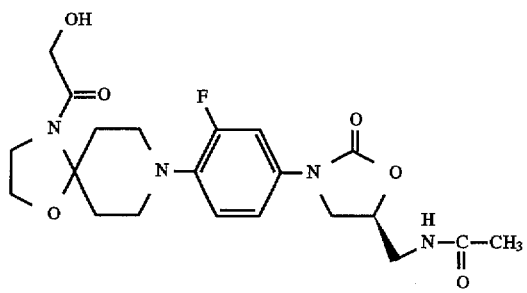

¹H NMR (DMSO-d₆) δ ppm: 1.52–1.57 (2H, m), 1.83 (3H, s), 2.73–2.92 (4H, m), 3.22–3.26 (2H, m), 3.38–3.42 (2H, m), 3.51–3.58 (2H, m), 3.67–3.73 (1H, m), 3.97–4.12 (5H, m), 4.62–4.75 (2H, m), 7.05–7.18 (2H, m), 7.47 (1H, dd, J=2.4, 15.1 Hz), 8.23 (1H, t, J=5.8 Hz).

Compound No. 59

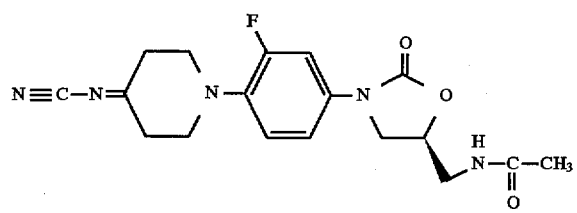

¹H NMR (DMSO-d₆) δ ppm: 1.83 (3H, s), 1.78–2.18 (4H, m), 3.10–3.21 (4H, m), 3.38 (2H, m), 3.70 (1H, dd, J=6.2, 9.2 Hz), 4.08 (1H, t, J=9.2 Hz), 4.71 (1H, m), 7.00–7.20 (2H, m), 7.48 (1H, dd, J=2.4, 14.0 Hz), 8.23 (1H, t, J=5.9 Hz).

Compound No. 60

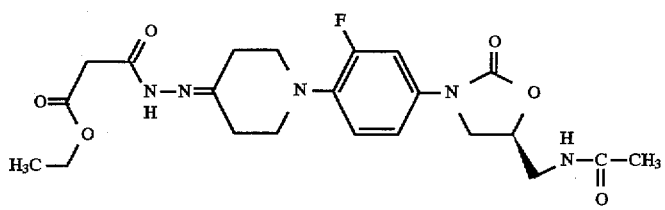

¹H NMR (CDCl₃) δ ppm: 1.27 and 1.32 (each, t, J=7.0H, total 3H), 2.02 (3H, s), 2.54–2.75 (4H, m), 3.15–3.26 (4H, m), 3.63–3.71 (2H, m), 3.76 (1H, dd, J=6.8, 9.3 Hz), 4.02 (1H, t, J=9.3 Hz), 4.21 and 4.25 (each q, J=7.0 Hz, total 2H), 4.77 (1H, m), 6.23 (1H, br s), 6.93 (1H, t, J=8.9 Hz), 7.07 (1H, dd, J=2.4, 8.9 Hz), 7.45 (1H, dd, J=2.4, 14.0 Hz).
Compound No. 61
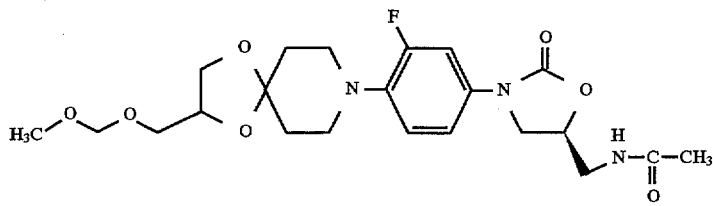
¹H NMR (CDCl₃) δ ppm: 1.85–1.97 (4H, m), 2.02 (3H, s), 3.09–3.18 (4H, m), 3.38 (3H, s), 3.54–3.84 (6H, m), 4.01 (1H, dd, J=9.0, 9.0 Hz), 4.12 (1H, dd, J=6.5, 8.4 Hz), 4.31–4.40 (1H, m), 4.67 (2H, s), 4.72–4.82 (1H, m), 6.15 (1H, br s), 6.94 (1H, dd, J=9.0, 9.0 Hz), 7.05 (1H, dd, J=1.9, 8.9 Hz), 7.40 (1H, dd, J=2.6, 14.2 Hz).
Compound No. 62
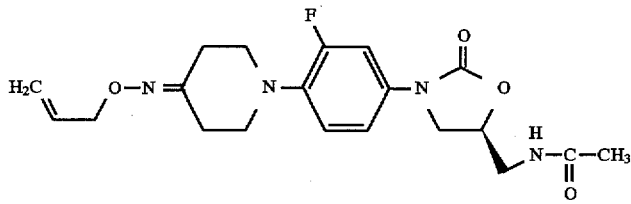
¹H NMR (CDCl₃) δ ppm: 2.02 (3H, s), 2.49–2.53 (2H, m), 2.77–2.81 (2H, m), 3.10–3.23 (4H, m), 3.56–3.78 (3H, m), 4.02 (1H, dd, J=8.6, 8.6 Hz), 4.56 (2H, dd, J=1.6, 5.9 Hz), 4.72–4.82 (1H, m), 5.22 (1H, dd, J=1.4, 10.8 Hz), 5.30 (1H, dd, J=1.4, 18.9 Hz), 5.94–6.08 (1H, m), 6.30 (1H, t, J=6.3 Hz), 6.92 (1H, dd, J=9.0, 9.0 Hz), 7.06 (1H, dd, J=2.4, 8.6 Hz), 7.43 (1H, dd, J=2.4, 14.0 Hz).
Compound No. 63
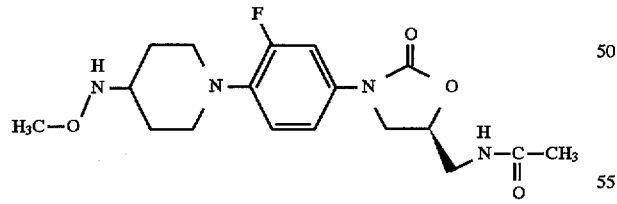

¹H NMR (CDCl₃) δ ppm: 1.54–1.68 (2H, m), 1.96–2.01 (2H, m), 2.02 (3H, s), 2.69–2.78 (2H, m), 2.96–3.07 (1H, m), 3.37–3.42 (2H, m), 3.57 (3H, s), 3.60–3.77 (3H, m), 4.01 (1H, dd, J=9.0, 9.0 Hz), 4.72–4.81 (1H, m), 6.22 (1H, t, J=5.8 Hz), 6.94 (1H, dd, J=9.0, 9.0 Hz), 7.05 (1H, dd, J=2.3, 9.0 Hz), 7.39 (1H, dd, J=2.3, 14.2 Hz).
Compound No. 64
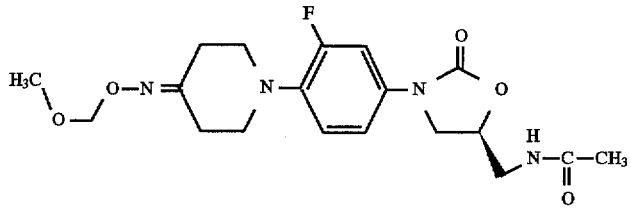
¹H NMR (CDCl₃) δ ppm: 2.02 (3H, s), 2.52–2.57 (2H, m), 2.79–2.83 (2H, m), 3.11–3.22 (4H, m), 3.44 (3H, s), 3.56–3.78 (3H, m), 4.02 (1H, dd, J=8.9, 8.9 Hz), 4.72–4.82 (1H, m), 5.09 (2H, s), 6.23 (1H, t, J=6.3 Hz), 6.93 (1H, dd, J=9.3, 9.3 Hz), 7.07 (1H, ddd, J=1.5, 1.5, 8.6 Hz), 7.44 (1H, dd, J=2.4, 14.0 Hz).
Compound No. 65
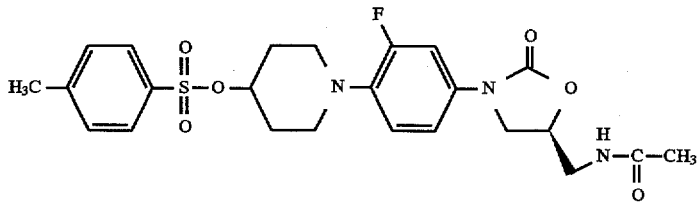
¹H NMR (CDCl₃) δ ppm: 1.91–2.02 (4H, m), 1.99 (3H, s), 2.46 (3H, s), 2.85–2.94 (2H, m), 3.15–3.23 (2H, m), 3.56–3.68 (2H, m), 3.74 (1H, dd, J=6.8, 9.3 Hz), 4.00 (1H, t, J=9.3 Hz), 7.04 (1H, dd, J=2.4, 9.5 Hz), 7.32 (2H, d, J=6.5 Hz), 7.40 (1H, dd, J=2.4, 14.0 Hz), 7.87 (2H, d, J=6.5 Hz).
Compound No. 66
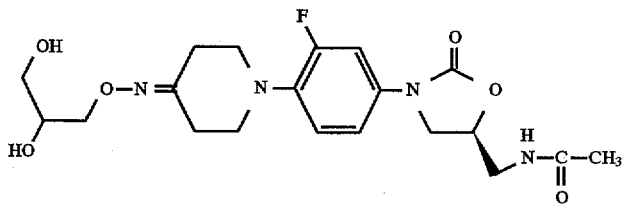
¹H NMR (DMSO-d₆) δ ppm: 1.83 (3H, s), 2.37–2.41 (2H, m), 2.64–2.68 (2H, m), 3.02–3.13 (4H, m), 3.34–3.42 (4H, m), 3.67–3.73 (2H, m), 3.86 (1H, dd, J=6.3, 10.7 Hz), 3.98 (1H, dd, J=5.0, 10.7 Hz), 4.08 (1H, dd, J=9.0, 9.0 Hz), 4.53 (1H, t, J=5.7 Hz), 4.68–4.75 (2H, m), 7.06–7.19 (2H, m), 7.49 (1H, dd, J=1.9, 14.6 Hz), 8.23 (1H, t, J=5.8 Hz).

Compound No. 67

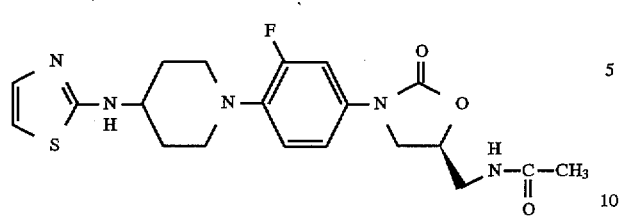

¹H NMR (DMSO-d₆) δ ppm: 1.54–1.60 (2H, m), 1.83 (3H, s), 1.80–2.00 (2H, m), 2.73 (2H, m), 3.16–3.34 (3H, m), 3.40 (2H, t, J=5.4 Hz), 3.70 (1H, dd, J=6.2, 9.2 Hz), 4.08 (1H, t, J=9.2 Hz), 4.70 (1H, m), 7.07 (1H, t, J=9.5 Hz), 7.16 (1H, dd, J=2.4, 9.5 Hz), 7.47 (1H, dd, J=2.4, 14.6 Hz), 7.97 (1H, d, J=9.7 Hz), 8.11 (1H, d, J=9.7 Hz), 8.23 (1H, t, J=5.9 Hz).

Compound No. 68

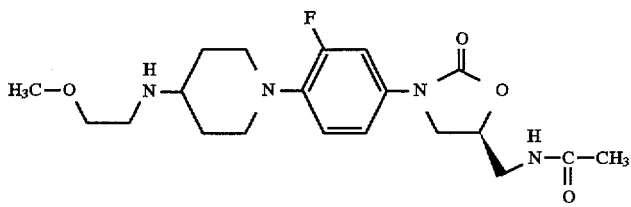

¹H NMR (DMSO-d₆) δ ppm: 1.32–1.43 (2H, m), 1.83 (3H, s), 1.86–1.90 (2H, m), 2.46–2.54 (1H, m), 2.62–2.70 (2H, m), 3.23–3.42 (6H, m), 3.33 (3H, s), 3.69 (1H, dd, J=6.3, 9.3 Hz), 4.07 (1H, dd, J=8.9, 8.9 Hz), 4.65–4.74 (1H, m), 7.02–7.17 (2H, m), 7.45 (1H, dd, J=2.4, 15.1 Hz), 8.23 (1H, t, J=5.5 Hz).

Compound No. 69

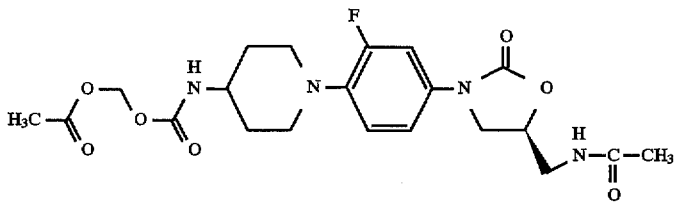

¹H NMR (DMSO-d₆) δ ppm: 1.51–1.63 (2H, m), 1.82–1.87 (2H, m), 1.83 (3H, s), 2.06 (3H, s), 2.66–2.74 (2H, m), 3.24–3.28 (2H, m), 3.38–3.50 (3H, m), 3.66–3.72 (1H, m), 4.07 (1H, dd, J=9.0, 9.0 Hz), 4.65–4.74 (1H, m), 5.63 (2H, s), 7.03–7.17 (2H, m), 7.46 (1H, dd, J=2.3, 15.0 Hz), 7.65 (1H, d, J=7.8 Hz), 8.23 (1H, t, J=5.7 Hz).

Compound No. 70

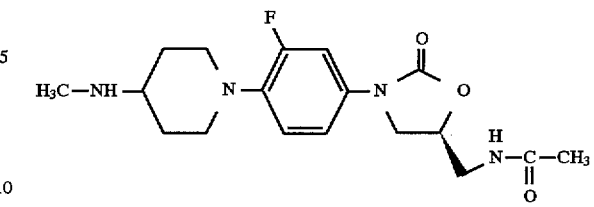

¹H NMR (DMSO-d₆) δ ppm: 1.31–1.45 (2H, m), 1.83 (3H, s), 1.84–1.90 (2H, m), 2.29 (3H, s), 2.31–2.44 (1H, m), 2.62–2.70 (2H, m), 3.23–3.28 (2H, m), 3.20–3.40 (1H, m), 3.38–3.42 (2H, m), 3.69 (1H, dd, J=6.3, 8.8 Hz), 4.07 (1H, dd, J=8.8, 8.8 Hz), 4.65–4.74 (1H, m), 7.02–7.17 (2H, m), 7.45 (1H, dd, J=2.4, 15.1 Hz), 8.23 (1H, t, J=5.9 Hz).

Compound No. 71

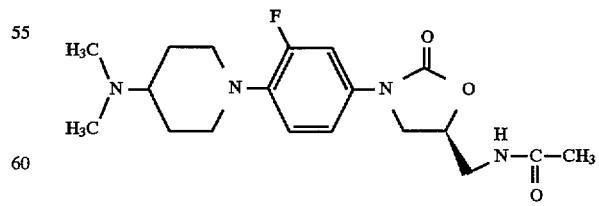

¹H NMR (DMSO-d₆) δ ppm: 1.46–1.59 (2H, m), 1.83–1.89 (2H, m), 1.88 (3H, s), 2.13–2.20 (1H, m), 2.19 (6H, s), 2.58–2.66 (2H, m), 3.28–3.35 (2H, m), 3.37–3.42 (2H, m), 3.69 (1H, dd, J=6.3, 9.3 Hz), 4.07 (1H, dd, J=8.8, 8.8 Hz), 4.65–4.74 (1H, m), 7.01–7.17 (2H, m), 7.45 (1H, dd, J=2.6, 14.7 Hz), 8.22 (1H, t, J=5.9 Hz).

Compound No. 72

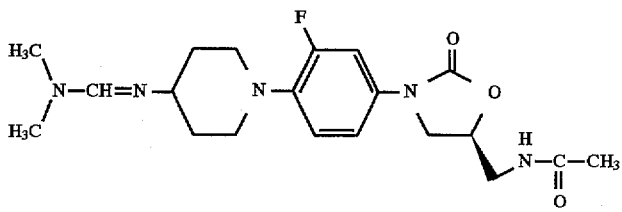

¹H NMR (CDCl₃) δ ppm: 1.74–1.86 (4H, m), 2.02 (3H, s), 2.71–2.80 (2H, m), 2.85 (6H, s), 3.05 (1H, m), 3.40–3.45 (2H, m), 3.60–3.76 (3H, m), 4.01 (1H, t, J=9.2 Hz), 4.77 (1H, m), 6.23 (1H, br s), 6.94 (1H, t, J=8.9 Hz), 7.05 (1H, dd, J=2.4, 8.9 Hz), 7.37 (1H, dd, J=2.4, 14.0 Hz), 7.38 (1H, s).

Compound No. 73

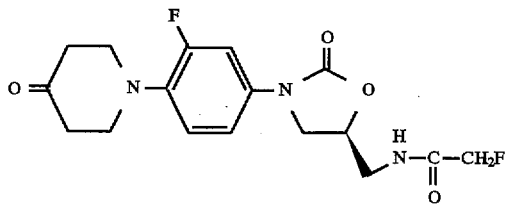

¹H NMR (CDCl₃) δ ppm: 2.62 (4H, t, J=5.7 Hz), 3.38 (4H, t, J=5.7 Hz), 3.49–3.89 (3H, m), 4.07 (1H, t, J=9.2 Hz), 4.74 (1H, d, J=1.6 Hz), 4.80 (1H, m), 4.92 (1H, d, J=1.6 Hz), 6.81 (1H, br s), 6.98 (1H, t, J=9.2 Hz), 7.10 (1H, dd, J=2.4, 9.2 Hz), 7.46 (1H, dd, J=2.4, 14.0 Hz).

Compound No. 74

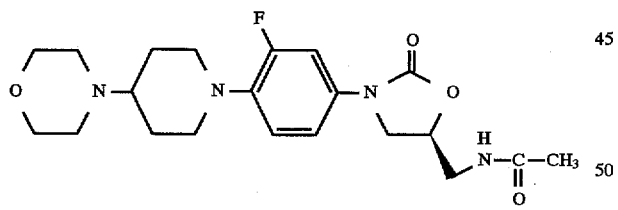

¹H NMR (DMSO-d₆) δ ppm: 1.54–1.61 (2H, m), 1.83 (3H, s), 1.80–2.00 (2H, m), 2.09–2.68 (8H, m), 3.30 (1H, m), 3.38 (2H, m), 3.50–3.58 (4H, m), 3.69 (1H, dd, J=6.8, 9.2 Hz), 4.05 (1H, t, J=9.2 Hz), 4.70 (1H, m), 7.05 (1H, t, J=9.5 Hz), 7.14 (1H, dd, J=2.4, 9.5 Hz), 7.45 (1H, dd, J=2.4, 14.6 Hz), 8.23 (1H, t, J=5.9 Hz).

We claim:

1. An oxazolidinone derivative represented by the general formula:

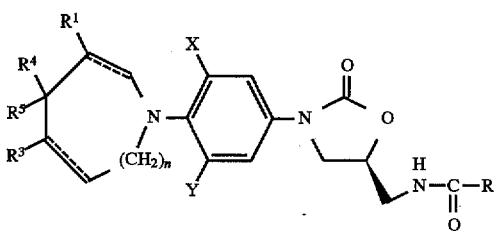

wherein
R is
 (a) hydrogen atom,
 (b) $C_1$–$C_8$ alkyl,
 (c) $C_3$–$C_6$ cycloalkyl,
 (d) amino,
 (e) $C_1$–$C_8$ alkylamino,
 (f) $C_1$–$C_8$ dialkylamino,
 (g) $C_1$–$C_8$ alkoxy, or
 (h) $C_1$–$C_8$ halogenoalkyl;
$R^1$ and $R^3$ are each and independently
 (a) hydrogen atom,
 (b) halogen atom,
 (c) $C_1$–$C_8$ alkyl,
 (d) $C_3$–$C_6$ cycloalkyl,
 (e) —(CH$_2$)$_m$—OR$^{11}$, or
 (f) —C(=O)—R$^{41}$;
X and Y are each and independently
 (a) hydrogen atom, or
 (b) halogen atom;
$R^4$ and $R^5$ are each and independently
 (a) hydrogen atom,
 (b) $C_1$–$C_8$ alkyl,
 (c) $C_1$–$C_8$ alkoxy,
 (d) $C_1$–$C_8$ alkylthio,
 (e) —(CH$_2$)$_m$—OR$^{51}$,
 (f) —O—(CH$_2$)$_m$—OR$^{51}$,
 (g) —NR$^{42}$R$^{52}$,
 (h) —N=CH—NR$^{44}$R$^{55}$,
 (i) —C(=O)—NR$^{42}$R$^{52}$, or
 (j) —(CH$_2$)$_m$—C(=A)—R$^{41}$,
or they may combine together to form
 (k) =O,
 (l) =NR$^{43}$,
 (m) =S,
 (n) =CR$^{44}$R$^{54}$, or
 (o) an optionally substituted, unsaturated or saturated 5- or 6-membered hetero ring having 1–3 hetero atoms selected from the group consisting of a nitrogen atom, an oxygen atom and a sulfur atom;
$R^{11}$ and $R^{12}$ are each and independently (a) hydrogen atom,
(b) $C_1$–$C_8$ alkyl, or
(c) methoxymethyl;

$R^{41}$ is
(a) hydrogen atom,
(b) —$(CH_2)_m$—OH,
(c) $C_1$–$C_8$ alkyl,
(d) $C_1$–$C_8$ alkoxy,
(e) —O—$CH_2$—O—C(=O)—$R^{11}$, or
(f) —$(CH_2)_m$—C(=O)—$OR^{11}$;

$R^{42}$ and $R^{52}$ are each and independently
(a) hydrogen atom,
(b) —$(CH_2)_m$—$OR^{11}$,
(c) $C_1$–$C_8$ alkyl,
(d) —C(=O)—$R^{41}$,
(e) —C(=O)—$NR^{11}R^{12}$,
(f) —$(CH_2)_p$-phenyl,
(g) thiazol-2-yl, or they may combine together to form a pyrrolidino group, a piperidino group, a piperazino group, a morpholino group, or a thiomorpholino group, each of which may be substituted by $C_1$–$C_8$ alkyl or —$(CH_2)_m$—OH;

$R^{43}$ is
(a) hydrogen atom,
(b) —$OR^{51}$,
(c) $C_1$–$C_8$ alkyl,
(d) $C_1$–$C_8$ alkoxy,
(e) —$(CH_2)_p$-phenyl,
(f) —$NR^{42}R^{52}$,
(g) —NH—C(=NH)—$NH_2$,
(h) [1,2,4]triazol-4-yl, or
(i) cyano;

$R^{44}$ and $R^{54}$ are each and independently
(a) hydrogen atom,
(b) $C_1$–$C_8$ alkyl,
(c) —C(=O)—$R^{41}$, or
(d) —$(CH_2)_p$-phenyl;

$R^{51}$ is
(a) hydrogen atom,
(b) $C_1$–$C_8$ alkyl,
(c) $C_1$–$C_8$ alkyl substituted by one or more hydroxy,
(d) $C_2$–$C_8$ alkenyl,
(e) $C_1$–$C_8$ halogenoalkyl,
(f) —$(CH_2)_m$—$OR^{11}$,
(g) —$(CH_2)_m$—C(=O)—$R^{41}$,
(h) —C(=O)—$(CH_2)_m$—$OR^{44}$, or
(i) tosyl;

A is
(a) oxygen atom, or
(b) ethyleneketal;

⸗ is a double bond or a single bond;
m's are each and independently 0, 1 or 2;
n is 0 or 1;
p's are each and independently 1, 2, 3 or 4;
and $C_1$–$C_8$ alkyl, in each of the above definitions, may be each and independently substituted by one or more substituents selected from the group consisting of a halogen atom, a hydroxy group, $C_1$–$C_8$ alkoxy group, $C_1$–$C_8$ acyloxy group, an amino group, $C_1$–$C_8$ alkylamino group, $C_1$–$C_8$ dialkylamino group, —CN group and a carboxyl group, or a pharmaceutically acceptable salt thereof.

2. The oxazolidinone derivative according to claim 1 wherein $R^4$ and $R^5$ combine together to form (a) =O,
(b) =$NR^{43}$ or a pharmaceutically acceptable salt thereof.

3. The oxazolidinone derivative according to claim 1, which is selected from the group consisting of:

(S)-1-{4-[5-(acetylamino-methyl)-2-oxo-oxazolidin-3-yl]-2-fluoro-phenyl}-piperidine-4-carboxylic acid ethyl ester, (S)-N-[3-(3-fluoro-4-piperidin-1-yl-phenyl)-2-oxo-oxazolidin-5-ylmethyl]-acetamide, (S)-N-{3-[3-fluoro-4-(4-hydroxy-piperidin-1-yl)-phenyl]-2-oxo-oxazolidin-5-ylmethyl}-acetamide, (S)-N-{3-[3-fluoro-4-(4-hydroxymethyl-piperidin-1-yl)-phenyl]-2-oxo-oxazolidin-5-ylmethyl}-acetamide, (S)-N-{3-[4-(4-dibenzylamino-piperidin-1-yl)-3-fluoro-phenyl]-2-oxo-oxazolidin-5-ylmethyl}-acetamide, (S)-N-{3-[4-(4-amino-piperidin-1-yl)-3-fluoro-phenyl]-2-oxo-oxazolidin-5-ylmethyl}-acetamide, (S)-N-{3-[3-fluoro-4-(4-oxo-piperidin-1-yl)-phenyl]-2-oxo-oxazolidin-5-ylmethyl}-acetamide, (S)-1-{4-[5-(acetylamino-methyl)-2-oxo-oxazolidin-3-yl]-2-fluoro-phenyl}-piperidine-4-carboxylic acid, (S)-N-{3-[4-(4-acetylamino-piperidin-1-yl)-3-fluoro-phenyl]-2-oxo-oxazolidin-5-ylmethyl}-acetamide, (S)-N-(1-{4-[5-(acetylamino-methyl)-2-oxo-oxazolidin-3-yl]-2-fluoro-phenyl}-piperidin-4-yl)-2-hydroxy-acetamide, (S)-N-{3-[3-fluoro-4-(4-hydroxyimino-piperidin-1-yl)-phenyl]-2-oxo-oxazolidin-5-ylmethyl}-acetamide, (S)-N-{3-[3-fluoro-4-(4-methoxymethoxy-piperidin-1-yl)-phenyl]-2-oxo-oxazolidin-5-ylmethyl}-acetamide, (S)-N-3-[4-(1,4-dioxa-8-aza-spiro[4.5]dec-8-yl)-3-fluoro-phenyl]-2-oxo-oxazolidin-5-ylmethyl)-acetamide, (S)-N-{3-[3-fluoro-4-(4-methoxyimino-piperidin-1-yl)-phenyl]-2-oxo-oxazolidin-5-ylmethyl)-acetamide, (S)-N-{3-[3-fluoro-4-(4-methoxycarbonylamino-piperidin-1-yl)-phenyl]-2-oxo-oxazolidin-5-ylmethyl}-acetamide, (S)-N-3-[3-fluoro-4-(4-methoxycarbonylhydrazono-piperidin-1-yl)-phenyl]-2-oxo-oxazolidin-5-ylmethyl}-acetamide, (S)-N-(3-{3-fluoro-4-[4-(2-methyl-[1,3]dioxolan-2-ylmethyl)-piperidin-1-yl]-phenyl}-2-oxo-oxazolidin-5-ylmethyl)-acetamide, (S)-N-(3-{3-fluoro-4-[4-(2-oxo-propyl)-piperidin-1-yl]-phenyl}-2-oxo-oxazolidin-5-ylmethyl)-acetamide, (S)-8-{4-[5-(acetylamino-methyl)-2-oxo-oxazolidin-3-yl]-2-fluoro-phenyl}-1,4-dioxa-8-aza-spiro[4.5]decane-6-carboxylic acid methyl ester, (S)-1-{4-[5-(acetylamino-methyl)-2-oxo-oxazolidin-3-yl]-2-fluoro-phenyl}-4-oxo-piperidin-3-carboxylic acid methyl ester, (S)-N-{3-[3-fluoro-4-(4-oxo-4H-pyridin-1-yl)-phenyl]-2-oxo-oxazolidin-5-ylmethyl}-acetamide, (S)-N-(3-{3-fluoro-4-[4-(2-methyl-[1,3]dioxolan-2-yl)-piperidin-1-yl]-phenyl}-2-oxo-oxazolidin-5-ylmethyl)-acetamide, (S)-N-{3-[4-(4-acetyl-piperidin-1-yl)-3-fluoro-phenyl]-2-oxo-oxazolidin-5-ylmethyl}-acetamide, (S)-N-{3-[3-fluoro-4-(3-hydroxymethyl-4-oxo-piperidin-1-yl)-phenyl]-2-oxo-oxazolidin-5-ylmethyl}-acetamide, (S)-N-{3-[3-fluoro-4-(4-methoxycarbonyloxyimino-piperidin-1-yl)-phenyl]-2-oxo-oxazolidin-5-ylmethyl}-acetamide, (S)-N-{3-[3-fluoro-4-(4-semicarbazono-piperidin-1-yl)-phenyl]-2-oxo-oxazolidin-5-ylmethyl}-acetamide, (S)-N -(3-{3-fluoro-4-[4-(morpholin-4-ylimino)-piperidin-1-yl]-phenyl}-2-oxo-oxazolidin-5-ylmethyl)-acetamide, (S)-N-[3-(3-fluoro-4-{4-[(2-hydroxy-ethyl)-hydrazono]-piperidin-1-yl}-phenyl)-2-oxo-oxazolidin-5-ylmethyl]-acetamide, (S)-N-{3-[3-fluoro-4-(4-amidinohydrazono-piperidin-1-yl)-phenyl]-2-oxo-oxazolidin-5-ylmethyl}-acetamide, (S)-N-{3-[3-fluoro-4-(4-acetoxyacetoxyimino-piperidin-1-yl)-phenyl]-2-oxo-oxazolidin-5-ylmethyl}-acetamide, (S)-N-(3-{3-fluoro-4-[4-(2-hydroxymethyl-[1,3]dioxolan-2-yl)-piperidin-1-yl]-phenyl}-2-oxo-oxazolidin-5-ylmethyl)-acetamide, (S)-N-{3-[3-fluoro-4-(4-benzyloxyacetoxyimino-piperidin-1-yl)-phenyl]-2-oxo-oxazolidin-5-ylmethyl}-acetamide, (S)-N-{3-[3-fluoro-4-(4-hydrazono-piperidin-1-yl)-phenyl]-2-oxo-oxazolidin-5-ylmethyl}-acetamide, (S)-(1-{4-[5-(acetylamino-methyl)-2-oxo-oxazolidin-3-yl]-2-fluoro-phenyl}-piperidin-4-ylideneaminooxy)-acetic acid methyl ester, (S)-N-(3-{3-fluoro-4-[4-(2-hydroxy-ethoxyimino)-piperidin-1-yl]-phenyl}-2-oxo-oxazolidin-5-ylmethyl)-acetamide, (S)-N-[3-(3-fluoro-4-{4-[4-(2-hydroxy-ethyl)-piperazin-1-ylimino]-piperidin-1-yl}-phenyl)-2-oxo-oxazolidin-5-ylmethyl]-acetamide, (S)-N-[3-(3-fluoro-4-{4-[(2-hydroxy-acetyl)-hydrazono]-piperidin-1-yl}-phenyl)-2-oxo-oxazolidin-5-ylmethyl]-acetamide, (S)-N-(3-{3-fluoro-4-[4-([1,2,4]triazol-4-ylimino)-piperidin-1-yl]-phenyl}-2-oxo-oxazolidin-5-ylmethyl)-acetamide, (S)-N-{3-[3-fluoro-4-(2-hydroxymethyl-1,4-dioxa-8-aza-spiro[4.5]dec-8-yl)-phenyl]-2-oxo-oxazolidin-5-ylmethyl}-acetamide, (S)-N-(3-{3-fluoro-4-[4-(2-methoxymethoxy-ethoxyimino)-piperidin-1-yl]-phenyl}-2-oxo-oxazolidin-5-ylmethyl)-acetamide, (S)-N-(3-{3-fluoro-4-[4-(2-hydroxy-acetyl)-1-oxa-4,8-diaza-spiro[4.5]dec-8-yl]-phenyl}-2-oxo-oxazolidin-5-ylmethyl)-acetamide, (S)-N-{3-[4-(4-cyanoimino-piperidin-1-yl)-3-fluoro-phenyl)-2-oxo-oxazolidin-5-ylmethyl}-acetamide, (S)-(1-{4-[5-(acetylamino-methyl)-2-oxo-oxazolidin-3-yl]-2-fluoro-phenyl}-piperidin-4-ylidenehydrazinocarbonyl)-acetic acid ethyl ester, (S)-N-(3-{3-fluoro-4-[2-(methoxymethoxy-methyl)-1,4-dioxa-8-aza-spiro[4.5]dec-8-yl]-phenyl}-2-oxo-oxazolidin-5-ylmethyl)-acetamide, (S)-N-{3-[4-(4-allyloxyimino-piperidin-1-yl)-3-fluoro-phenyl]-2-oxo-oxazolidin-5-ylmethyl}-acetamide, (S)-N-{3-[3-fluoro-4-(4-methoxyarnino-piperidin-1-yl)-phenyl]-2-oxo-oxazolidin-5-ylmethyl}-acetamide, (S)-N-{3-[3-fluoro-4-(4-methoxymethoxyimino-piperidin-1-yl)-phenyl]-2-oxo-oxazolidin-5-ylmethyl}-acetamide, toluene-4-sulfonic acid (S)-1-{4-[5-(acetylamino-methyl)-2-oxo-oxazolidin-3-yl]-2-fluoro-phenyl}-piperidin-4-yl ester, (S)-N-(3-{4-[4-(2,3-dihydroxy-propoxyimino)-piperidin-1-yl]-3-fluoro-phenyl}-2-oxo-oxazolidin-5-ylmethyl)-acetamide, (S)-N-(3-{3-fluoro-4-[4-(thiazol-2-ylamino)-piperidin-1-yl]-phenyl}-2-oxo-oxazolidin-5-ylmethyl)-acetamide, (S)-N-(3-{3-fluoro-4-[4-(2-methoxy-ethylamino)-piperidin-1-yl]-phenyl}-2-oxo-oxazolidin-5-ylmethyl)-acetamide, (S)-N-(3-{4-[4-(acetoxy-methoxy-carbonylamino)-piperidin-1-yl]-3-fluorophenyl}-2-oxo-oxazolidin-5-ylmethyl)-acetamide, (S)-N-{3-[3-fluoro-4-(4-methylamino-piperidin-1-yl)-phenyl]-2-oxo-oxazolidin-5-ylmethyl}-acetamide, (S)-N-{3-[4-(4-dimethylamino-piperidin-1-yl)-3-fluoro-phenyl]-2-oxo-oxazolidin-5-ylmethyl}-acetamide, (S)-N-{3-[4-(4-dimethylaminomethyleneamino-piperidin-1-yl)-3-fluoro-phenyl]-2-oxo-oxazolidin-5-ylmethyl}-acetamide, (S)-2-fluoro-N-{3-[3-fluoro-4-(4-oxo-piperidin-1-yl)-phenyl]-2-oxo-oxazolidin-5-ylmethyl}-acetamide and (S)-N-{3-[3-fluoro-4-(4-morpholin-4-yl-piperidin-1-yl)-phenyl]-2-oxo-oxazolidin-5-ylmethyl}-acetamide or a pharmaceutically acceptable salt thereof.

4. An antimicrobial agent comprising an oxazolidinone derivative according to claim 1 or a pharmaceutically acceptable salt thereof as an effective ingredient.

5. An antimicrobial agent comprising an oxazolidinone derivative according to claim 2 or a pharmaceutically acceptable salt thereof as an effective ingredient.

* * * * *